United States Patent [19]

Takeo et al.

[11] Patent Number: 5,732,121

[45] Date of Patent: Mar. 24, 1998

[54] METHOD FOR DETECTING ABNORMAL PATTERNS

[75] Inventors: Hideya Takeo; Nobuyoshi Nakajima, both of Kanagawa-ken, Japan

[73] Assignee: Fuji Photo Film Co., Ltd., Kanagawa-Ken, Japan

[21] Appl. No.: 731,001

[22] Filed: Oct. 9, 1996

[30] Foreign Application Priority Data

Oct. 11, 1995 [JP] Japan .................................. 7-263281
Jan. 26, 1996 [JP] Japan .................................. 8-011885

[51] Int. Cl.⁶ .................................................. G01N 23/04
[52] U.S. Cl. .................................................. 378/62; 250/584
[58] Field of Search ........................ 378/37, 62; 250/584

[56] References Cited

U.S. PATENT DOCUMENTS

| | | | |
|---|---|---|---|
| 4,991,092 | 2/1991 | Greensite | 382/131 |
| 5,157,733 | 10/1992 | Takeo et al. | 382/6 |
| 5,481,623 | 1/1996 | Hara | 382/128 |
| 5,583,346 | 12/1996 | Hakajima | 250/587 |

OTHER PUBLICATIONS

"Detection of Tumor Patterns in DR Images (Iris Filter)", Obata et al., Collected Papers of the Institute of Electronics and Communication Engineers of Japan, D-II, J75-D-II, No. 3, pp. 663–670, Mar. 1992.

*Primary Examiner*—David P. Porta
*Assistant Examiner*—David Vernon Bruce
*Attorney, Agent, or Firm*—Sughrue, Mion, Zinn, Macpeak & Seas, PLLC

[57] ABSTRACT

Prospective abnormal patterns in a radiation image of an object are detected in accordance with an image signal representing the radiation image. A probability density function of the image signal, which corresponds to a region, that is inward from a contour of each of the prospective abnormal patterns having been detected, and a neighboring region, is formed. Probability density function information in accordance with the probability density function is obtained. A definite prospective abnormal pattern, which is among the prospective abnormal patterns having been detected and has a high level of probability that it will be the true abnormal pattern, is detected in accordance with the probability density function information.

18 Claims, 10 Drawing Sheets

| $f_7$ | $f_6$ | $f_5$ | $f_4$ | $f_3$ |
| --- | --- | --- | --- | --- |
| $f_8$ |  |  |  | $f_2$ |
| $f_9$ |  | PICTURE ELEMENT j |  | $f_1$ |
| $f_{10}$ |  |  |  | $f_{16}$ |
| $f_{11}$ | $f_{12}$ | $f_{13}$ | $f_{14}$ | $f_{15}$ |

| i\j | 0 | 1 | 2 | 3 | 4 | 5 | 6 | 7 | 8 | 9 | 10 |
|---|---|---|---|---|---|---|---|---|---|---|---|
| 0 | 1 | | | | | | | | | | |
| 1 | | 1 | | | | | | | | | |
| 2 | | | | | | | | | | | |
| 3 | | | | | | | | | | | |
| 4 | | | | | | | | | | | |
| 5 | | | | 2 | | | | | | | |
| 6 | | | | | | | | | | | |
| 7 | | | | | | | | | | | |
| 8 | | | | | | | | | | | |
| 9 | | | | | | | | | | | |
| 10 | | | | | | | | | | | |

F I G .13
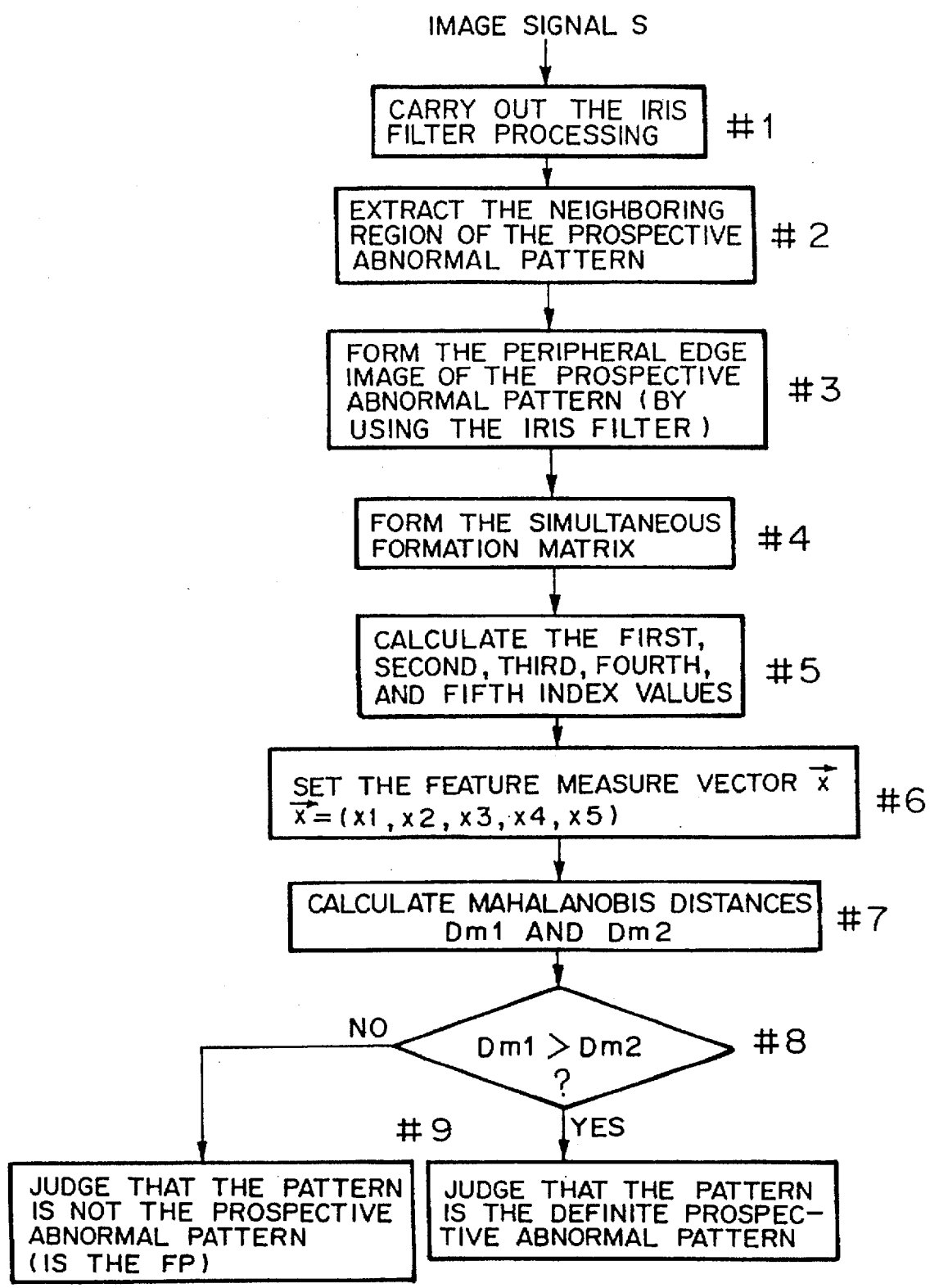

METHOD FOR DETECTING ABNORMAL PATTERNS

BACKGROUND OF THE INVENTION

1. Field of the Invention

This invention relates to a method for detecting an abnormal pattern, typically a tumor pattern, in a radiation image, wherein prospective abnormal patterns in the radiation image are detected. This invention particularly relates to a method for detecting an abnormal pattern wherein, of the prospective abnormal patterns having been detected, only a definite prospective abnormal pattern is detected.

2. Description of the Prior Art

Image processing, such as gradation processing or frequency processing, has heretofore been carried out on an image signal, which represents an image and has been obtained with one of various image obtaining methods, such that a visible image having good image quality can be reproduced and used as an effective tool in, particularly, the accurate and efficient diagnosis of an illness. Particularly, in the field of medical images, such as radiation images of human bodies serving as objects, it is necessary for specialists, such as doctors, to make an accurate diagnosis of an illness or an injury of the patient in accordance with the obtained image. Therefore, it is essential to carry out the image processing in order that a visible image having good image quality can be reproduced and used as an effective tool in the accurate and efficient diagnosis of an illness.

In such image processing, the processing is often carried out on the entire area of the image. Alternatively, in cases where the purpose of examination or diagnosis is clear to a certain extent, the emphasis processing is often carried out selectively on a desired image portion, which is adapted to the purpose of examination or diagnosis.

Ordinarily, when an image portion to be processed is to be selected, the person, who views the radiation image, views the original image before being processed and manually selects the image portion to be processed. However, there is the risk that the selected image portion or the specified image range will vary, depending upon the level of the experience or the image understanding capability of the person, who views the radiation image, and the selection cannot be carried out objectively.

For example, in cases where a radiation image has been recorded for the examination of breast cancer, it is necessary to find a tumor pattern, which is one of features of a cancerous portion, from the radiation image. However, the range of the tumor pattern cannot always be specified accurately. Therefore, there is a strong demand for techniques for objectively detecting an abnormal pattern, such as a tumor pattern, without depending upon the skill of the person, who views the radiation image.

As one of the techniques for satisfying the aforesaid demand, iris filter processing (hereinbelow often referred to as the operation of the iris filter) has heretofore been proposed. [Reference should be made to "Detection of Tumor Patterns in DR images (Iris Filter)," Obata, et al., Collected Papers of The Institute of Electronics and Communication Engineers of Japan, D-II, Vol. j75-D-II, No. 3, pp. 663–670, March 1992.] The iris filter processing has been studied as a technique efficient for detecting, particularly, a tumor pattern, which is one of characteristic forms of mammary cancers. However, the image to be processed with the iris filter is not limited to the tumor pattern in a mammogram, and the iris filter processing is applicable to any kind of image portion having the characteristics such that the gradients of the image signal representing the image are centralized.

How the processing for detecting the image portion with the iris filter is carried out will be described hereinbelow by taking the processing for the detection of the tumor pattern as an example.

It has been known that, for example, in a radiation image recorded on X-ray film (i.e., an image yielding an image signal of a high signal level for a high image density), the image density values of a tumor pattern are slightly smaller than the image density values of the surrounding image areas. The image density values of the tumor pattern are distributed such that the image density value becomes smaller from the periphery of an approximately circular tumor pattern toward the center point of the tumor pattern. Thus the distribution of the image density values of the tumor pattern has gradients of the image density values. Therefore, in the tumor pattern, the gradients of the image density values can be found in local areas, and the gradient lines (i.e., gradient vectors) centralize in the directions heading toward the center point of the tumor pattern.

The iris filter calculates the gradients of image signal values, which are represented by the image density values, as gradient vectors and feeds out the information representing the degree of centralization of the gradient vectors. With the iris filter processing, a tumor pattern is detected in accordance with the degree of centralization of the gradient vectors.

Specifically, the gradient vector at an arbitrary picture element in a tumor pattern is directed to the vicinity of the center point of the tumor pattern. On the other hand, in an elongated pattern, such as a blood vessel pattern, gradient vectors do not centralize upon a specific point. Therefore, the distributions of the directions of the gradient vectors in local areas may be evaluated, and a region, in which the gradient vectors centralize upon a specific point, may be detected. The thus detected region may be taken as a prospective tumor pattern, which is considered as being a tumor pattern. The processing with the iris filter is based on such fundamental concept. Steps of algorithms of the iris filter will be described hereinbelow.

(Step 1) Calculation of gradient vectors

For each picture element j among all of the picture elements constituting a given image, the direction $\theta$ of the gradient vector of the image signal representing the image is calculated with Formula (1).

$$\theta = \tan^{-1} \frac{(f_3+f_4+f_5+f_6+f_7)-(f_{11}+f_{12}+f_{13}+f_{14}+f_{15})}{(f_1+f_2+f_3+f_{15}+f_{16})-(f_7+f_8+f_9+f_{10}+f_{11})} \quad (1)$$

As illustrated in FIG. 3, $f_1$ through $f_{16}$ in Formula (1) represent the picture element values (i.e., the image signal values) corresponding to the picture elements located at the peripheral areas of a mask, which has a size of five picture elements (located along the column direction of the picture element array)×five picture elements (located along the row direction of the picture element array) and which has its center at the picture element j.

(Step 2) Calculation of the degree of centralization of gradient vectors

Thereafter, for each picture element among all of the picture elements constituting the given image, the picture element is taken as a picture element of interest, and the degree of centralization C of the gradient vectors with respect to the picture element of interest is calculated with Formula (2).

$$C = (1/N) \sum_{j=1}^{N} \cos\theta_j \qquad (2)$$

As illustrated in FIG. 4, in Formula (2), N represents the number of the picture elements located in the region inside of a circle, which has its center at the picture element of interest and has a radius R, and θj represents the angle made between the straight line, which connects the picture element of interest and each picture element j located in the circle, and the gradient vector at the picture element j, which gradient vector has been calculated with Formula (1). Therefore, in cases where the directions of the gradient vectors of the respective picture elements j centralize upon the picture element of interest, the degree of centralization C represented by Formula (2) takes a large value.

The gradient vector of each picture element j, which is located in the vicinity of a tumor pattern, is directed approximately to the center portion of the tumor pattern regardless of the level of the contrast of the tumor pattern. Therefore, it can be regarded that the picture element of interest associated with the degree of centralization C, which takes a large value, is the picture element located at the center portion of the tumor pattern. On the other hand, in a linear pattern, such as a blood vessel pattern, the directions of the gradient vectors are biased to a certain direction, and therefore the value of the degree of centralization C is small. Accordingly, a tumor pattern can be detected by taking each of all picture elements, which constitute the image, as the picture element of interest, calculating the value of the degree of centralization C with respect to the picture element of interest, and rating whether the value of the degree of centralization C is or is not larger than a predetermined threshold value. Specifically, the processing with the iris filter has the features over an ordinary difference filter in that the processing with the iris filter is not apt to be adversely affected by blood vessel patterns, mammary gland patterns, or the like, and can efficiently detect tumor patterns.

In actual processing, such that the detection performance unaffected by the sizes and shapes of tumor patterns may be achieved, it is contrived to adaptively change the size and the shape of the filter. FIG. 5 shows an example of the filter. The filter is different from the filter shown in FIG. 4. With the filter of FIG. 5, the degree of centralization is rated only with the picture elements, which are located along radial lines extending radially from a picture element of interest in M kinds of directions at 2π/M degree intervals. (In FIG. 5, by way of example, 32 directions at 11.25 degree intervals are shown.)

In cases where the picture element of interest has the coordinates (k, 1), the coordinates ([x], [y]) of the picture element, which is located along an i'th radial line and is the n'th picture element as counted from the picture element of interest, are given by Formulas (3) and (4).

$$x = k + n\cos\{2\pi(i-1)/M\} \qquad (3)$$

$$y = l + n\sin\{2\pi(i-1)/M\} \qquad (4)$$

wherein [x] represents the maximum integer, which does not exceed x, and [y] represents the maximum integer, which does not exceed y.

Also, for each of the radial lines, the output value obtained for the picture elements ranging from a certain picture element to a picture element, which is located along the radial line and at which the maximum degree of centralization is obtained, is taken as the degree of centralization Cimax with respect to the direction of the radial line. The mean value of the degrees of centralization Cimax, which have been obtained for all of the radial lines, is then calculated. The mean value of the degrees of centralization Cimax having thus been calculated is taken as the degree of centralization C of the gradient vector group with respect to the picture element of interest.

Specifically, the degree of centralization Ci(n), which is obtained for the picture elements ranging from the picture element of interest to the n'th picture element located along the i'th radial line, is calculated with Formula (5).

$$Ci(n) = \sum_{l=1}^{n} \{(\cos\theta_{il})/n\}, \; Rmin \leq n \leq Rmax \qquad (5)$$

wherein Rmin and Rmax respectively represent the minimum value and the maximum value having been set for the radius of the tumor pattern, which is to be detected.

Specifically, with Formula (5), the degree of centralization Ci(n) is calculated with respect to all of the picture elements, which are located along each of the radial lines and fall within the range from the picture element of interest, that is located on each radial line, to a picture element, that is located at a length of distance falling within the range from a length of distance corresponding to the minimum value Rmin having been set for the radius of the tumor pattern to be detected to a length of distance corresponding to the maximum value Rmax.

Thereafter, the degree of centralization C of the gradient vector group is calculated with Formulas (6) and (7).

$$Ci_{max} = \max_{Rmin \leq n \leq Rmax} Ci(n) \qquad (6)$$

$$C = (1/32) \sum_{i=1}^{32} Ci_{max} \qquad (7)$$

The value of Cimax of Formula (6) represents the maximum value of the degree of centralization Ci(n) obtained for each of the radial lines with Formula (5). Therefore, the region from the picture element of interest to the picture element associated with the degree of centralization Ci(n), which takes the maximum value, may be considered as being the region of the prospective tumor pattern along the direction of the radial line.

The calculation with Formula (6) is made for all of the radial lines, and the regions of the prospective tumor pattern on all of the radial lines are thereby detected. The regions of the prospective tumor pattern on the adjacent radial lines are then connected by a straight line or a non-linear curve. In this manner, it is possible to specify the shape of the peripheral edge of the region, which may be regarded as the prospective tumor pattern.

Thereafter, with Formula (7), the mean value of the maximum values Cimax of the degrees of centralization within the aforesaid regions, which maximum values Cimax have been given by Formula (6) for all directions of the radial lines, is calculated. In Formula (7), by way of example, the radial lines are set along 32 directions. The calculated mean value is compared with a predetermined threshold value T, which is appropriate for making a judgment as to whether the detected pattern is or is not a prospective tumor pattern. From the results of the comparison, a judgment is made as to whether there is or is not a probability that the region having its center at the picture element of interest will be the abnormal pattern.

The size and the shape of the region, in which the degree of centralization C of the gradient vector group with Formula (7) is rated, change adaptively in accordance with the distribution of the gradient vectors. Such an adaptive change is similar to the manner, in which the iris of the human's eye expands or contracts in accordance with the brightness of the external field. Therefore, the aforesaid technique for detecting the region of the prospective tumor pattern by utilizing the degrees of centralization of the gradient vectors is referred to as the iris filter processing.

The calculation of the degree of centralization $Ci(n)$ may be carried out by using Formula (5') in lieu of Formula (5).

$$Ci(n) = \frac{1}{n - Rmin + 1} \sum_{l=Rmin}^{n} \cos\theta_{il}, \quad Rmin \leq n \leq Rmax \quad (5')$$

Specifically, with Formula (5'), the degree of centralization $Ci(n)$ is calculated with respect to all of the picture elements, which are located along each of the radial lines and fall within the range from a picture element, that is located at a length of distance corresponding to the minimum value Rmin having been set for the radius of the tumor pattern to be detected, the length of distance being taken from the picture element of interest located on each radial line, to a picture element, that is located at a length of distance falling within the range from the length of distance corresponding to the minimum value Rmin to a length of distance corresponding to the maximum value Rmax, the length of distance being taken from the picture element of interest located on each radial line.

By carrying out the steps described above, the iris filter can efficiently detect only the tumor pattern, which has a desired size, from a radiation image. Research has heretofore been carried out on the iris filter particularly for the purpose of detecting a cancerous portion from a mammogram.

As described above, with the iris filter processing, tumor patterns can be detected efficiently. However, all of the patterns having been detected with the iris filter processing are not necessarily the tumor patterns representing breast cancer. Specifically, with the iris filter processing, the detection is carried out on the basis of only the image density gradients and the size of the region to be detected. Therefore, all of the image portions, that have sizes coinciding with the size of the region to be detected and have certain levels of image density gradients, are detected regardless of whether the detected image portions are or are not the tumor patterns. For example, an image portion, at which two blood vessel patterns intersect each other, has a size coinciding with the desired size and has certain levels of the degrees of centralization of the image density gradients. Therefore, such an image portion is often detected with the iris filter processing. Thus the iris filter processing serves to merely detect prospective abnormal patterns, instead of detecting only the truly abnormal patterns.

Accordingly, when the iris filter processing is to be used in practice, it is necessary that only the more definite prospective abnormal pattern, i.e. the prospective abnormal pattern which has a very high level of probability that it will be the true abnormal pattern, can be detected ultimately. Specifically, of the image portions having been detected as the prospective abnormal patterns, the image portions (hereinbelow referred to as the "false positives" or FP), which are actually not the abnormal patterns, should be eliminated.

SUMMARY OF THE INVENTION

The primary object of the present invention is to provide a method for detecting an abnormal pattern wherein, of the prospective abnormal patterns having been detected with the processing for detecting prospective abnormal patterns, such as iris filter processing, only the prospective abnormal pattern, which has a high level of probability that it will be the true abnormal pattern, is detected ultimately.

A true abnormal pattern, particularly a tumor pattern representing breast cancer, has the characteristics such that it may have a low image density (a high luminance) and approximately uniform image density values (signal values) in the region of the pattern. In view of such characteristics, in a first method for detecting an abnormal pattern in accordance with the present invention, wherein prospective abnormal patterns are detected with the processing for detecting prospective abnormal patterns, such as iris filter processing, probability density function information of the image signal, which corresponds to a region inward from a contour of each of the prospective abnormal patterns and a neighboring region, is obtained, and only the prospective abnormal pattern, which has a high level of probability that it will be the true abnormal pattern, is detected in accordance with the probability density function information.

Specifically, the present invention provides a first method for detecting an abnormal pattern in a radiation image, wherein prospective abnormal patterns in a radiation image of an object are detected (with iris filter processing, or the like) in accordance with an image signal representing the radiation image, the method comprising the steps of:

i) forming a probability density function of the image signal, which corresponds to a region, that is inward from a contour of each of the prospective abnormal patterns having been detected, and a neighboring region, ii) obtaining probability density function information in accordance with the probability density function, and iii) detecting a definite prospective abnormal pattern, which is among the prospective abnormal patterns having been detected (with the iris filter processing, or the like), in accordance with the probability density function information.

For example, in order for the definite prospective abnormal pattern to be detected in accordance with the probability density function information, the probability density function information may be compared with a predetermined threshold value, and the definite prospective abnormal pattern may be detected on the basis of the results of the comparison. Alternatively, the probability density function information having been obtained for a prospective abnormal pattern and the probability density function information having been obtained for a different prospective abnormal pattern may be compared with each other, and the definite prospective abnormal pattern may be detected on the basis of the results of the comparison.

By way of example, as the probability density function information, it is possible to employ at least one index value selected from the group consisting of a first index value representing a variance, var, of the probability density function, which variance is calculated with Formula (9), a second index value representing a contrast, con, of the probability density function, which contrast is calculated with Formula (10), and a third index value representing an angular moment, asm, of the probability density function, which angular moment is calculated with Formula (11).

$$var = \sum^{N} \{(S - \bar{S})^2 \cdot P(S)\} \quad (9)$$

$$con = \sum^{N} \{S^2 \cdot P(S)\} \quad (10)$$

$$asm = \sum^{N} \{P(S)\}^2 \quad (11)$$

wherein $\bar{S}$ represents the mean value of the image density values S within the region, and N represents the number of picture elements falling within the region.

In cases where the definite prospective abnormal pattern is to be detected by comparing the probability density function information and the threshold value with each other, as for at least one index value selected from the group consisting of the first, second, and third index values, a threshold value is set. For example, a first threshold value, a second threshold value, and a third threshold value may be set which respectively correspond to the first, second, and third index values. The first, second, and third index values may then be respectively compared with the first, second, and third threshold values. On the basis of the results of the comparisons, the definite prospective abnormal pattern may be detected.

Specifically, in cases where only the first index value is selected for the comparison from the first, second, and third index values, only the first threshold value may be set. The first index value and the first threshold value may be compared with each other, and the definite prospective abnormal pattern may be detected on the basis of the results of the comparison. In cases where two index values are selected for the comparison, only the two threshold values corresponding to the two index values may be set. The two index values may be compared respectively with the corresponding threshold values, and the definite prospective abnormal pattern may be detected on the basis of the results of the comparisons. In cases where three index values are selected for the comparison, three threshold values corresponding to the three index values may be set. The three index values may be compared respectively with the corresponding threshold values, and the definite prospective abnormal pattern may be detected on the basis of the results of the comparisons.

As described above, in the first method for detecting an abnormal pattern in accordance with the present invention, the threshold values corresponding to the index values may be set, the index values and the corresponding threshold values may be compared with each other, and the definite prospective abnormal pattern may be detected on the basis of the results obtained by gathering the results of the respective comparisons. Alternatively, a new rating function value may be obtained by defining at least two index values, which are selected from the aforesaid three index values, with a predetermined weight function, and the definite prospective abnormal pattern may be detected in accordance with the rating function value.

As the rating function value defined with the weight function, for example, a Mahalanobis distance or a Fisher discriminating function may be employed.

Specifically, in general, the region of a detected prospective abnormal pattern is expressed in terms of an n-dimensional space with the form of $x=(x1, x2, x3, \ldots, xn)$ by using n-order feature measures $x1, x2, x3, \ldots, xn$. The n-dimensional axes are referred to as the feature axes. More specifically, the values (the aforesaid index values), which are obtained from the feature extraction, are the values xi (where $i=1, 2, \ldots, n$) on the respective feature axes.

One of important properties, which the n-dimensional pattern space formed by the feature extraction step, is that the similarity of the patterns, which are given as the inputs, with respect to each other should be kept appropriately in the pattern space. Specifically, if the pattern space does not have the properties such that similar patterns may take positions close to each other in the pattern space, there is no sense in carrying out the feature extraction. Therefore, the concept of distance is introduced into the pattern space.

Various functions (distance functions) for expressing the concept of distance have been proposed. Typical examples of the function values include the Euclidean distance, the Mahalanobis distance, the city block distance, the chess board distance, and the Minkowski distance. The most simplest function value is the Euclidean distance. However, the Euclidean distance does not take the state of the spread of the pattern into consideration, and therefore it is considered that the Euclidean distance is not suitable for the method for detecting an abnormal pattern in accordance with the present invention.

Therefore, it is preferable that the most basic Mahalanobis distance is employed, and the state of spread of the pattern is taken into consideration.

The term "Mahalanobis distance" means the distance, Dmi, which is defined by Formula (17) shown below. The Mahalanobis distance is measured from the center point of the distribution and with the weighting of a hyper-ellipsoid expressed by a covariance matrix $\Sigma$.

$$Dmi=(\vec{x}-\vec{mi})t\Sigma_i^{-1}(\vec{x}-\vec{mi}) \qquad (17)$$

wherein $\Sigma i$ represents the covariance matrix of the pattern class (pattern classification between the normal pattern of $i=1$ and the abnormal pattern of $i=2$) wi, i.e., $$\Sigma_i = (1/Ni) \sum_{x \in w1} (\vec{x}-\vec{mi})(\vec{x}-\vec{mi})^t$$

t represents the transposed vector (row vector), $\vec{x}$ represents the vector of the feature measure x, i.e., $$\vec{x}=(x1, x2, \ldots, xN)$$

$\Sigma i^{-1}$ represents the inverse matrix of $\Sigma i$, and $\vec{mi}$ represents the mean value of the pattern classes wi, i.e., $$\vec{mi} = (1/Ni) \sum_{x \in w1} \vec{x}$$

Specifically, the steps described below are carried out:

1) The respective index values described above are calculated with respect to the region of the prospective abnormal pattern which is to be detected.

2) The feature measure vector $\vec{x}=(x1, x2, \ldots, xn)$ is defined in accordance with each index value.

3) The Mahalanobis distance Dm1 with respect to the pattern class (i=1), which represents the normal pattern (FP) and has been obtained experimentally, and the Mahalanobis distance Dm2 with respect to the pattern class (i=2), which represents the abnormal pattern and has been obtained experimentally, are calculated with Formula (17). 4) The Mahalanobis distances Dm1 and Dm2 are compared with each other. In cases where the Mahalanobis distance Dm1 with respect to the pattern class, which represents the normal pattern, is shorter than the Mahalanobis distance Dm2 with respect to the pattern class, which represents the abnormal pattern, i.e. in cases where Dm1<Dm2, it is judged that the pattern is the normal pattern. In cases where the Mahalanobis distance Dm2 with respect to the pattern class, which represents the abnormal pattern, is shorter than the Mahalanobis distance Dm1 with respect to the pattern class, which represents the normal pattern, i.e. in cases where Dm1>Dm2, it is judged that the pattern is the abnormal pattern. Only the patterns having been judged as being the abnormal pattern are detected.

As described above, in cases where the Mahalanobis distance is employed as the rating function value, instead of the rating function value and the threshold value being compared with each other, the rating function values are compared with each other. The detection of the abnormal pattern is carried out on the basis of the results of the comparison.

As the rating function value defined with the aforesaid weight function, the value of the Fisher discriminating function can also be employed.

The Fisher discriminating function is defined by Formula (18) shown below.

$$J(\vec{w}) = (|\vec{m}1 - \vec{m}2|)^2 / (\Sigma_1^2 + \Sigma_2^2) \tag{18}$$

wherein $\Sigma 1$ represents the covariance matrix of the pattern class of the normal pattern, $\Sigma 2$ represents the covariance matrix of the pattern class of the abnormal pattern, $$\vec{m}1 = (1/Ni) \sum_{x \in w1} \vec{x}$$

and $$\vec{m}2 = (1/Ni) \sum_{x \in w2} \vec{x}$$

When Formula (18) takes the maximum value, the degree of separation between the two classes, i.e. the class 1 (the normal pattern) and the class 2 (the abnormal pattern), becomes highest. Specifically, when $$\Sigma_w = \Sigma_1 + \Sigma_2 \tag{19}$$

the value of $\vec{w}$, which maximizes $J(\vec{w})$, is given by $$\vec{w} = \Sigma_w^{-1} (\vec{m}1 - \vec{m}2) \tag{20}$$

Therefore, the scalar quantity of Formula (21)

$$z = [\vec{w}^t \cdot \vec{x}]$$

is calculated from the N-dimensional feature measure vector $\vec{x}$, and a judgment with the threshold value is carried out in accordance with the distribution of the scalar quantity.

More specifically, the steps described below are carried out:

1) The respective index values described above are calculated with respect to the region of the prospective abnormal pattern which is to be detected.

2) The feature measure vector $x = (x1, x2, \ldots, xn)$ is defined in accordance with each index value.

3) The scalar quantity expressed as $$z = [\vec{w}^t \cdot \vec{x}]$$

is calculated with Formula (21). The value of $\vec{w}$ is calculated previously.

4) The obtained scalar quantity z is processed with the threshold value, and a judgment is made as to whether the pattern is the normal pattern or the abnormal pattern. Only the patterns having been judged as being the abnormal pattern are detected.

The distribution and the level of the scalar quantity z vary for different combinations of the feature measures employed. For example, in cases where the scalar quantity z has the distribution and the level shown in FIG. 12, the threshold value of the level shown in FIG. 12 may be set.

As described above, in cases where the value of the Fisher discriminating function is employed as the rating function value, the detection of the abnormal pattern is carried out on the basis of the results of the comparison of the rating function value and the threshold value with each other.

A true abnormal pattern, particularly a tumor pattern representing breast cancer, has the characteristics such that the contour (i.e., the periphery) of the pattern has an approximately circular shape. In view of such characteristics, in a second method for detecting an abnormal pattern in accordance with the present invention, wherein prospective abnormal patterns are detected with the processing for detecting prospective abnormal patterns, such as iris filter processing, edge information of a contour of each of the prospective abnormal patterns is obtained, and only the prospective abnormal pattern, which has a high level of probability that it will be the true abnormal pattern, is detected in accordance with the edge information.

Specifically, the present invention also provides a second method for detecting an abnormal pattern in a radiation image, wherein prospective abnormal patterns in a radiation image of an object are detected (with iris filter processing, or the like) in accordance with an image signal representing the radiation image, the method comprising the steps of:

i) obtaining edge information of a contour of each of the prospective abnormal patterns having been detected, and ii) detecting a definite prospective abnormal pattern, which is among the prospective abnormal patterns having been detected (with the iris filter processing, or the like), in accordance with the edge information.

For example, in order for the definite prospective abnormal pattern to be detected in accordance with the edge information, the edge information may be compared with a predetermined threshold value, and the definite prospective abnormal pattern may be detected on the basis of the results of the comparison. Alternatively, the edge information having been obtained for a prospective abnormal pattern and the edge information having been obtained for a different prospective abnormal pattern may be compared with each other, and the definite prospective abnormal pattern may be detected on the basis of the results of the comparison.

By way of example, as the edge information, it is possible to employ at least one index value selected from the group consisting of a first index value representing a variance with respect to a simultaneous formation matrix having been obtained by the utilization of iris filter processing, which variance is calculated with Formula (12), a second index value representing a difference entropy with respect to the simultaneous formation matrix, which difference entropy is calculated with Formula (13), a third index value representing a correlation with respect to the simultaneous formation matrix, which correlation is calculated with Formula (14), a fourth index value representing an inverse difference moment with respect to the simultaneous formation matrix, which inverse difference moment is calculated with Formula (15), and a fifth index value representing a sum entropy with respect to the simultaneous formation matrix, which sum entropy is calculated with Formula (16).

$$var = \sum_i \sum_j \{(i - \mu_x)^2 \cdot P_g(i, j)\} \tag{12}$$

$$dfe = \sum_k \{P_{x-y}(k) \cdot \log|P_{x-y}(k)|\} \tag{13}$$

$$cor = \sum_i \sum_j [\{i \cdot j \cdot P_g(i, j) - \mu_x \cdot \mu_y\} / (\sigma_x, \sigma_y)] \tag{14}$$

-continued $$idm = \sum_i \sum_j [P_g(i,j)/\{1+(i-j)^2\}] \quad (15)$$

$$se = -\sum_k [P_{x+y}(k) \cdot \log\{P_{x+y}(k)\}] \quad (16)$$

wherein $$\mu_x = \sum_i \{i \cdot P_x(i)\}, \mu_y = \sum_j \{j \cdot P_y(j)\}$$

$$P_{x-y}(k) = \sum_i \sum_j P_g(i,j), k = |i-j|$$

$$P_{x+y}(k) = \sum_i \sum_j P_g(i,j), k = i+j$$

$$\sigma_x^2 = \sum_i (i-\mu_x)^2 \cdot P_x(i)$$

$$\sigma_y^2 = \sum_j (j-\mu_y)^2 \cdot P_y(j)$$

$P_x(i)$ represents the projection distribution along the j direction, i.e., $$P_x(i) = \sum_j P_g(i,j)$$

and $Py(j)$ represents the projection distribution along the i direction, i.e., $$P_y(j) = \sum_i P_g(i,j)$$

In cases where the definite prospective abnormal pattern is to be detected by comparing the edge information and the threshold value with each other, as for at least one index value selected from the group consisting of the first, second, third, fourth, and fifth index values, a threshold value is set. For example, a first threshold value, a second threshold value, a third threshold value, a fourth threshold value, and a fifth threshold value may be set which respectively correspond to the first, second, third, fourth, and fifth index values. The first, second, third, fourth, and fifth index values may then be respectively compared with the first, second, third, fourth, and fifth threshold values. On the basis of the results of the comparisons, the definite prospective abnormal pattern may be detected.

Specifically, in cases where only the first index value is selected for the comparison from the first, second, third, fourth, and fifth index values, only the first threshold value may be set. The first index value and the first threshold value may be compared with each other, and the definite prospective abnormal pattern may be detected on the basis of the results of the comparison. In cases where three index values are selected for the comparison, only the three threshold values corresponding to the three index values may be set. The three index values may be compared respectively with the corresponding threshold values, and the definite prospective abnormal pattern may be detected on the basis of the results of the comparisons. In cases where five index values are selected for the comparison, five threshold values corresponding to the five index values may be set. The five index values may be compared respectively with the corresponding threshold values, and the definite prospective abnormal pattern may be detected on the basis of the results of the comparisons.

As described above, in the second method for detecting an abnormal pattern in accordance with the present invention, the threshold values corresponding to the index values may be set, the index values and the corresponding threshold values may be compared with each other, and the definite prospective abnormal pattern may be detected on the basis of the results obtained by gathering the results of the respective comparisons. Alternatively, a new rating function value may be obtained by defining at least two index values, which are selected from the aforesaid five index values, with a predetermined weight function, and the definite prospective abnormal pattern may be detected in accordance with the rating function value.

As the rating function value defined with the weight function, for example, the Mahalanobis distance or the Fisher discriminating function described above may be employed. The Mahalanobis distance and the Fisher discriminating function can be applied in the same manner as that described above with reference to the first method for detecting an abnormal pattern in accordance with the present invention.

In a third method for detecting an abnormal pattern in accordance with the present invention, the aforesaid first and second methods for detecting an abnormal pattern in accordance with the present invention are combined with each other. The probability density function information and the edge information are obtained, and the definite prospective abnormal pattern is detected in accordance with them.

Specifically, the present invention further provides a third method for detecting an abnormal pattern in a radiation image, wherein prospective abnormal patterns in a radiation image of an object are detected in accordance with an image signal representing the radiation image, the method comprising the steps of:

i) forming a probability density function of the image signal, which corresponds to a region, that is inward from a contour of each of the prospective abnormal patterns having been detected, and a neighboring region, ii) obtaining probability density function information in accordance with the probability density function, iii) obtaining edge information of a contour of each of the prospective abnormal patterns having been detected, and iv) detecting a definite prospective abnormal pattern, which is among the prospective abnormal patterns having been detected, in accordance with the probability density function information and the edge information.

In the third method for detecting an abnormal pattern in accordance with the present invention, the definite prospective abnormal pattern is detected in accordance with the probability density function information and the edge information. For example, the detection in accordance with the probability density function information and the detection in accordance with the edge information may be carried out independently, and the definite prospective abnormal pattern may be detected ultimately on the basis of the results of the detections. Alternatively, a new rating function value may be obtained by defining the probability density function information and the edge information by using a predetermined weight function, and the definite prospective abnormal pattern may be detected in accordance with the rating function value. As the rating function value defined with the weight function, for example, the Mahalanobis distance or the Fisher discriminating function described above may be employed.

By way of example, as the probability density function information, it is possible to employ at least one index value selected from the group consisting of a first index value representing the variance, var, of the probability density function, which variance is calculated with Formula (9), a second index value representing the contrast, con, of the probability density function, which contrast is calculated with Formula (10), and a third index value representing the angular moment, asm, of the probability density function, which angular moment is calculated with Formula (11). Also, by way of example, as the edge information, it is possible to employ at least one index value selected from the group consisting of a fourth index value representing the variance with respect to the simultaneous formation matrix having been obtained by the utilization of iris filter processing, which variance is calculated with Formula (12), a fifth index value representing the difference entropy with respect to the simultaneous formation matrix, which difference entropy is calculated with Formula (13), a sixth index value representing the correlation with respect to the simultaneous formation matrix, which correlation is calculated with Formula (14), a seventh index value representing the inverse difference moment with respect to the simultaneous formation matrix, which inverse difference moment is calculated with Formula (15), and an eighth index value representing the sum entropy with respect to the simultaneous formation matrix, which sum entropy is calculated with Formula (16).

As described above, a true abnormal pattern, particularly a tumor pattern representing breast cancer, has the characteristics such that it may have a low image density and approximately uniform image density values (signal values) in the region of the pattern. In view of such characteristics, with the first method for detecting an abnormal pattern in accordance with the present invention, wherein prospective abnormal patterns are detected with the processing for detecting prospective abnormal patterns, such as iris filter processing, the probability density function information of the image signal, which corresponds to the region inward from the contour of each of the prospective abnormal patterns and the neighboring region, is obtained and processed with the threshold value. In this manner, only the prospective abnormal pattern, which has a high level of probability that it will be the true abnormal pattern, can be detected accurately.

Also, as described above, a true abnormal pattern, particularly a tumor pattern representing breast cancer, has the characteristics such that the contour of the pattern has an approximately circular shape. In view of such characteristics, with the second method for detecting an abnormal pattern in accordance with the present invention, wherein prospective abnormal patterns are detected with the processing for detecting prospective abnormal patterns, such as iris filter processing, the edge information of the contour of each of the prospective abnormal patterns is obtained and processed with the threshold value. In this manner, only the prospective abnormal pattern, which has a high level of probability that it will be the true abnormal pattern, can be detected accurately.

With the third method for detecting an abnormal pattern in accordance with the present invention, the aforesaid first and second methods for detecting an abnormal pattern in accordance with the present invention are combined with each other. Therefore, the same effects as those of the aforesaid first and second methods for detecting an abnormal pattern in accordance with the present invention can be obtained.

BRIEF DESCRIPTION OF THE DRAWINGS

FIG. 13 is a flow chart showing the processing steps in an embodiment of the method for detecting an abnormal pattern in accordance with the present invention, wherein a rating function value is utilized.

DESCRIPTION OF THE PREFERRED EMBODIMENTS

The present invention will hereinbelow be described in further detail with reference to the accompanying drawings.

Figure 1:
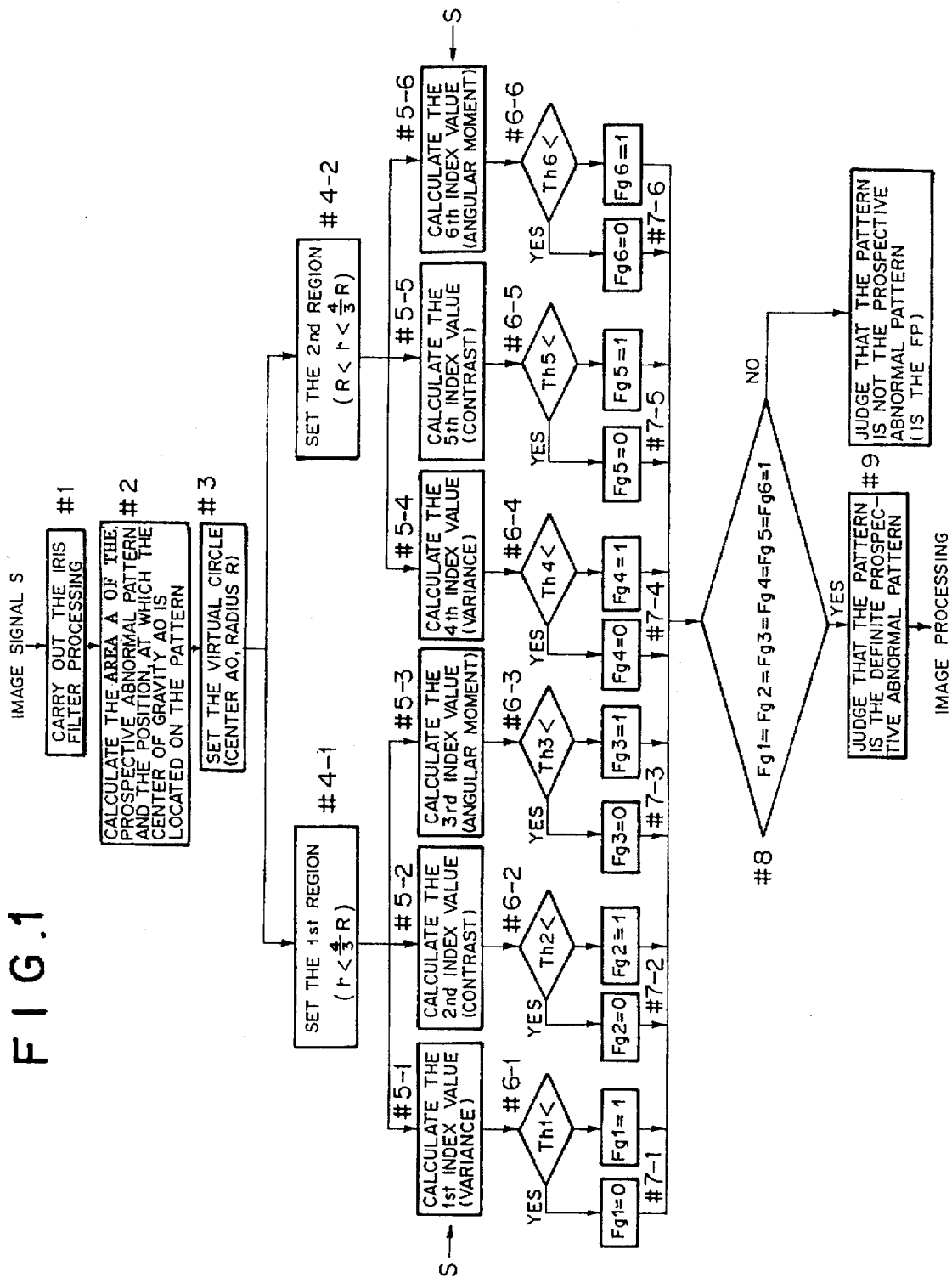
FIG. 1 is a flow chart showing the processing steps in a first embodiment of the method for detecting an abnormal pattern in accordance with the present invention.

FIG. 1 is a flow chart showing the processing steps in a first embodiment of the method for detecting an abnormal pattern in accordance with the present invention.

In this embodiment, an image signal is employed, which represents a radiation image recorded on film and which has a high signal level for a high image density, i.e. which represents the image density values (a large image density value for an image of a high image density, and a small image density value for an image of a low image density).

Figure 2A:
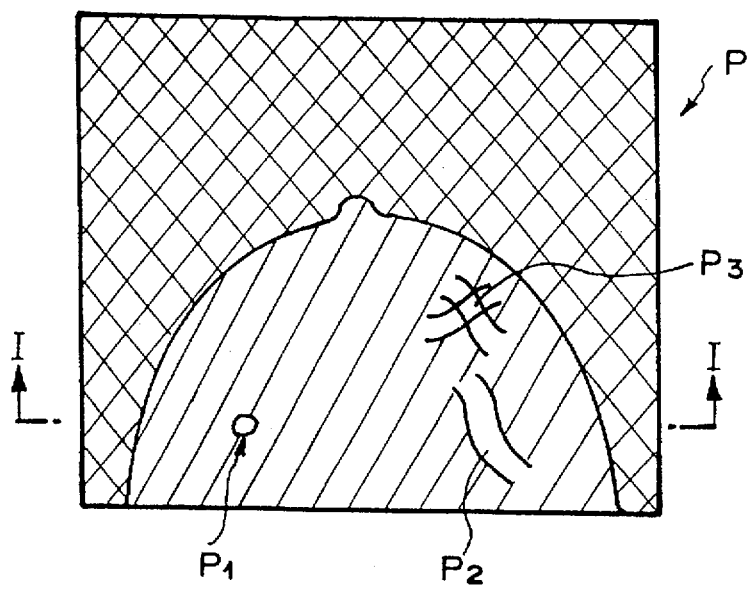
FIG. 2A is an explanatory view showing a radiation image of the mamma (i.e., a mammogram), which is subjected to the detection of an abnormal pattern carried out with the embodiment of FIG. 1.

In this embodiment, in a first step (#1), an image signal, which represents a radiation image of an object (in this case, the mamma) P shown in FIG. 2A and represents image density values S, is received from an image read-out apparatus (not shown), or the like, and iris filter processing is carried out on the image density values S. With the iris filter processing, an image portion (a tumor pattern) $P_1$, which represents breast cancer, or the like, in the radiation image is detected.

How the iris filter processing is carried out will be described hereinbelow.

Firstly, for each picture element j among all of the picture elements constituting the radiation image, a calculation is made with Formula (1) shown below. In this manner, the direction θ of the gradient vector of the image density value S (i.e., the image density gradient vector) is calculated.

$$\theta = \tan^{-1}\frac{(f_3+f_4+f_5+f_6+f_7)-(f_{11}+f_{12}+f_{13}+f_{14}+f_{15})}{(f_1+f_2+f_3+f_{15}+f_{16})-(f_7+f_8+f_9+f_{10}+f_{11})} \quad (1)$$

Figures 3, 4:
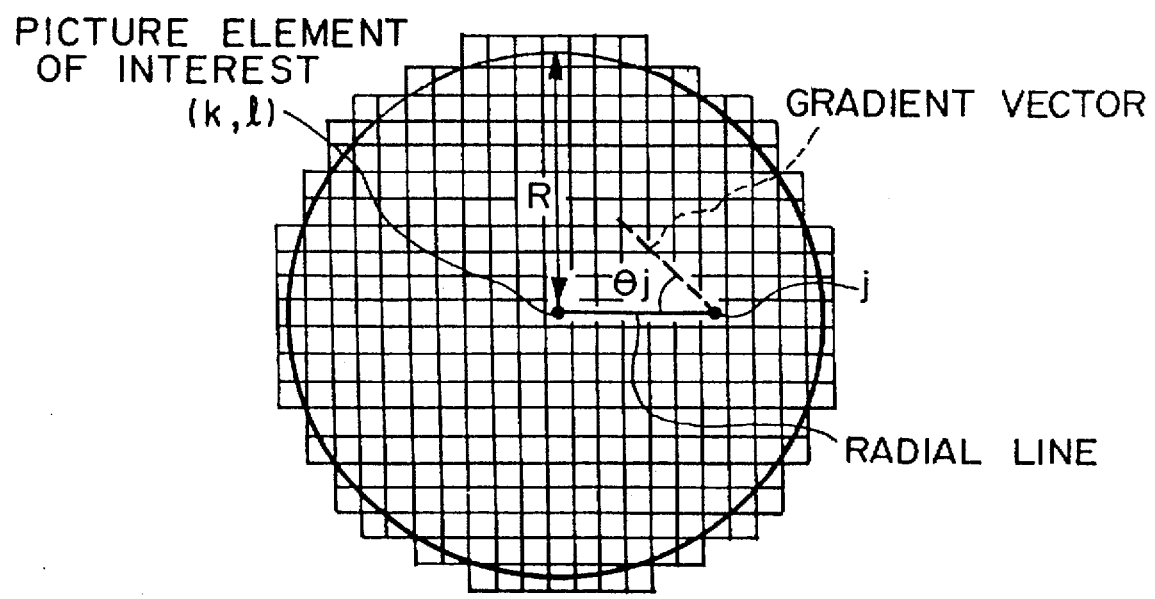
FIG. 3 is an explanatory view showing a mask, which is used for calculating directions of gradient vectors in iris filter processing.
FIG. 4 is an explanatory view showing the concept behind the degree of centralization of a gradient vector with respect to a picture element of interest.
Figure 5:
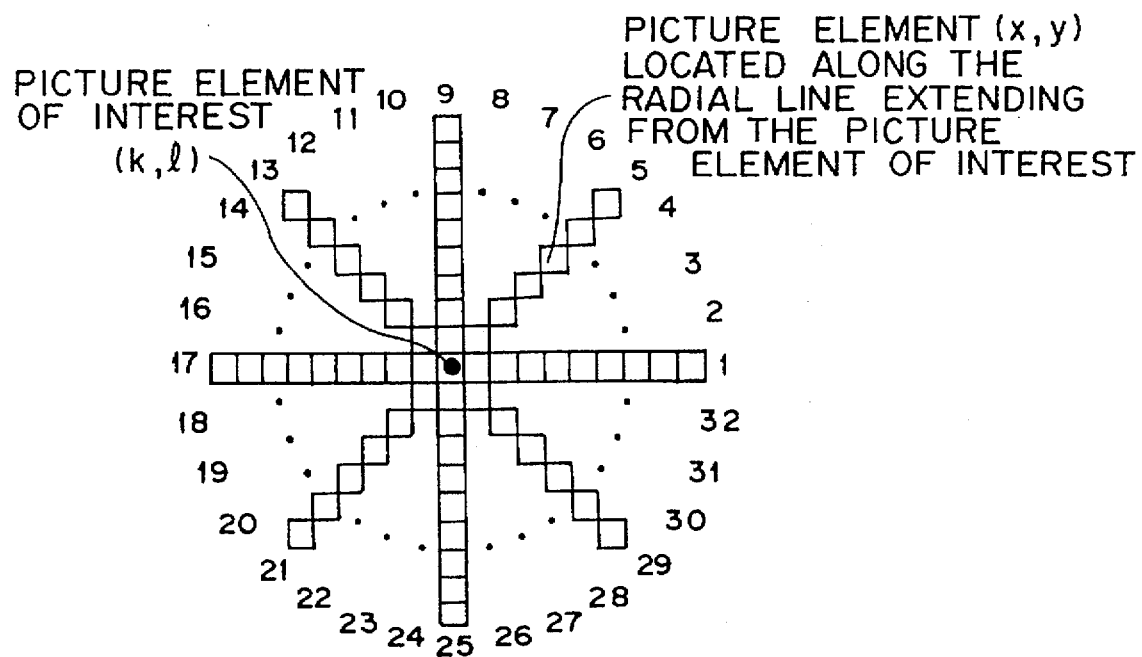
FIG. 5 is an explanatory view showing the concept behind an iris filter, which is set such that a contour shape may change adaptively.

As illustrated in FIG. 3, $f_1$ through $f_{16}$ in Formula (1) represent the image density values S corresponding to the picture elements located at the peripheral areas of a mask, which has a size of 5×5 picture elements and has its center at the picture element j. The size of the mask is not limited to 5×5 picture elements.

In this manner, for each picture element among all of the picture elements constituting the radiation image, the directions θ of the image density gradient vectors in the vicinity of the picture element is calculated. Thereafter, a picture element is found, upon which the directions of the image density gradient vectors centralize.

Specifically, for each picture element among all of the picture elements constituting the radiation image, the picture element is taken as a picture element of interest, and the degree of centralization C of the image density gradient vectors with respect to the picture element of interest is calculated with Formula (2).

$$C = (1/N) \sum_{j=1}^{N} \cos\theta_j \quad (2)$$

As illustrated in FIG. 4, in Formula (2), N represents the number of the picture elements located in the region inside of a circle, which has its center at the picture element of interest and has a radius R, and θj represents the angle made between the straight line, which connects the picture element of interest and each picture element j located in the circle, and the image density gradient vector at the picture element j, which gradient vector has been calculated with Formula (1). The right side of Formula (2) represents the degree, with Which the directions θj of the image density gradient vectors at all picture elements falling within the circle having the radius of R coincide with the directions heading from the respective picture elements toward the picture element of interest. Specifically, the right side of Formula (2) represents the degree of centralization C of the image density gradient vectors. Therefore, in cases where the directions of the gradient vectors of the respective picture elements j centralize upon the picture element of interest, the degree of centralization C represented by Formula (2) takes a large value.

Figure 2B:
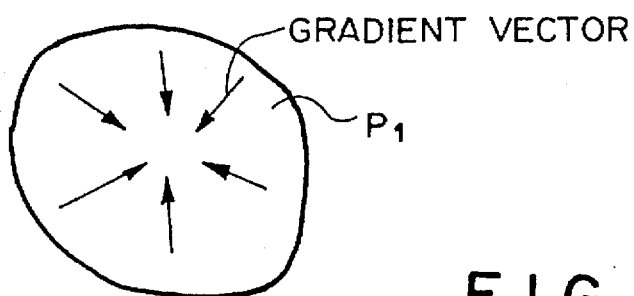
FIG. 2B is an explanatory view showing the degree of centralization of gradient vectors in a tumor pattern.
Figure 2C:
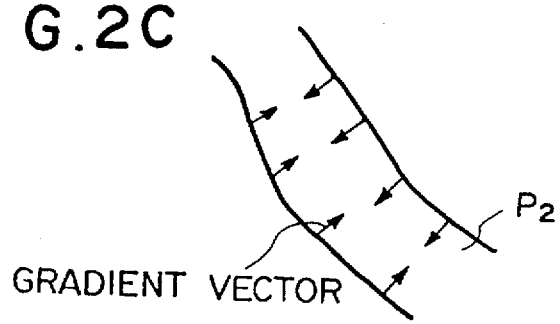
FIG. 2C is an explanatory view showing the degree of centralization of gradient vectors in a blood vessel pattern, or the like, FIG. 2D is an explanatory view showing the degree of centralization of gradient vectors in a portion at which two blood vessel patterns, or the like, intersect each other.

The degree of centralization C of the image density gradient vectors is thus calculated for the reasons described below. Specifically, the tumor pattern representing breast cancer in the radiation image (negative) has the characteristics such that the image density values at the center point of the tumor pattern are smaller than the image density values of the surrounding image areas (i.e., the center point is lighter than the surrounding image areas). The image density values of the tumor pattern are distributed such that the image density value becomes larger from the center point of the tumor pattern toward the periphery of the tumor pattern. Therefore, by the rating of the degree of centralization C, the tumor pattern $P_1$ shown in FIG. 2B and a blood vessel or mammary gland pattern $P_2$ shown in FIG. 2C can be discriminated from each other.

With the iris filter processing, the processing is then carried out with Formulas (3) through (7) shown above. With the processing, the effects described above are obtained.

Figure 2D:
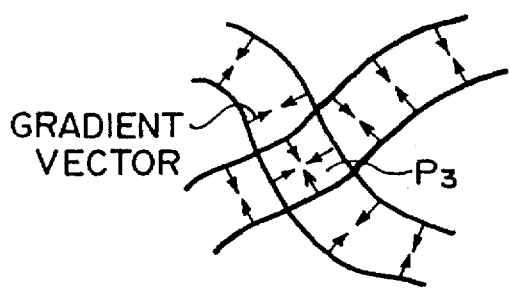

In this manner, with the iris filter processing for rating the degree of centralization C of the image density gradient vectors, only the tumor pattern $P_1$ can be detected efficiently. However, for example, as illustrated in FIG. 2D, in a pattern $P_3$ of a portion at which two blood vessel patterns intersect each other (hereinbelow referred to as the false positive $P_3$), the degree of centralization C takes a large value as in the tumor pattern $P_1$. Therefore, it often occurs that the detection of only the tumor pattern $P_1$ cannot be carried out.

Specifically, with the iris filter processing in the step 1 (#1), not only the tumor pattern $P_1$, which is to be detected, but also the false positive $P_3$, which is not to be detected, is detected.

Therefore, in this embodiment, only the tumor pattern $P_1$ is separated and detected with the processing of a step 2 (#2) and those that follow. The processing is based upon the characteristics of the tumor pattern such that the contour of the tumor pattern has a shape close to a circle, and such that the image density values in the region inside of the tumor pattern are more uniform than in the other regions and are small.

In the step 2 (#2), for each of the tumor pattern $P_1$ and the false positive $P_3$ having been detected with the iris filter processing, the area A of the pattern and the center of gravity AO on the pattern are calculated.

Figure 6:
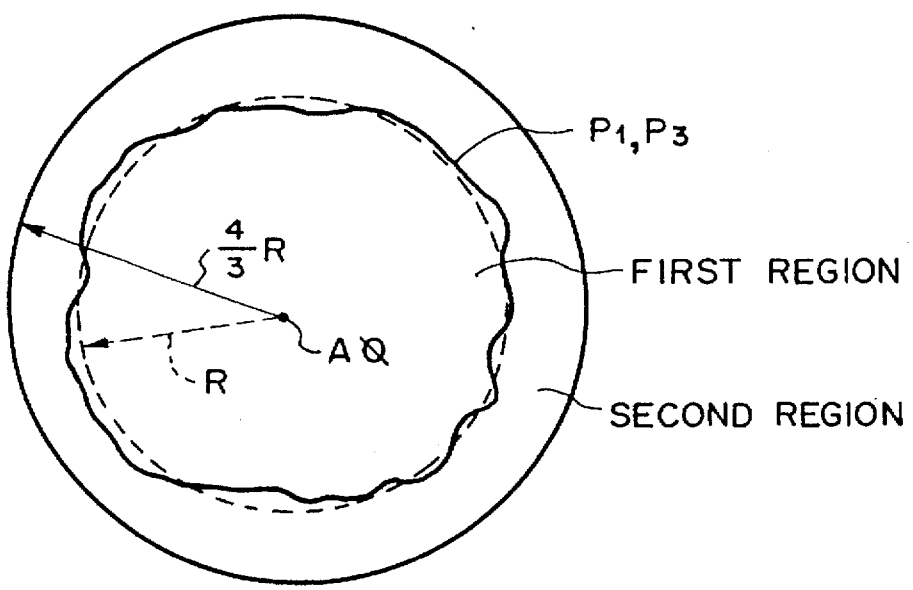
FIG. 6 is an explanatory view showing a virtual circle, which has a radius R and an area approximately equal to the area A of a prospective abnormal pattern having been obtained with iris filter processing, a first region, which is a region inward from a virtual circle having a radius of 4R/3, and a second region, which is a doughnut-like annular region sandwiched between an inner circle having a radius larger than the radius R and an outer circle having a radius smaller than 4R/3.

Thereafter, in a step 3 (#3), as illustrated in FIG. 6, a virtual circle is set. The virtual circle has an area approximately equal to the area A of the pattern, has its center at the position at which the center of gravity AO is located, and has a radius R calculated with Formula (8).

$$R = (A/\pi)^{1/2} \quad (8)$$

Also, in a step 4-1 (#4-1), with respect to the virtual circle having the radius R, a first region (r<4R/3) is set, which is a region inward from a virtual circle having a radius of 4R/3. Further, in a step 4-2 (#4-2), with respect to the virtual circle having the radius R, a second region (R<r<4R/3) is set, which is a doughnut-like annular region sandwiched between an inner circle having a radius larger than the radius R and an outer circle having a radius smaller than 4R/3. The first region corresponds to the internal region containing the contour of the pattern. The second region corresponds to the contour of the pattern.

The processing described below is carried out on each of the first and second regions.

Firstly, the probability density function of the image density values S (for example, in the cases of 10-bit notation, values of 0 to 1,023) of each region is formed. The frequency of each image density value S is represented by P(S). In accordance with the distribution of the frequencies P(S) with respect to the image density values S, the probability density function information of each region is calculated.

Specifically, as for the first region, in steps 5-1 (#5-1, 5-2 (#5-2), and 5-3 (#5-3), calculations are made to find, respectively, (i) a first index value, var, which represents the variance and is calculated with Formula (9), (ii) a second index value, con, which represents the contrast and is calculated with Formula (10), and (iii) a third index value, asm, which represents the angular moment and is calculated with Formula (11). Also, as for the second region, in steps 5-4 (#5-4), 5-5 (#5-5), and 5-6 (#5-6), fourth, fifth, and sixth index values, which correspond respectively to the first, second, and third index values described above for the first region, are calculated.

$$var = \sum^{N} \{(S - \bar{S})^2 \cdot P(S)\} \quad (9)$$

$$con = \sum^{N} \{S^2 \cdot P(S)\} \quad (10)$$

$$asm = \sum^{N} \{P(S)\}^2 \quad (11)$$

wherein $\bar{S}$ represents the mean value of the image density values S within the region, and N represents the number of picture elements falling within the region.

The first (or fourth) index value, var, represents the state of spread of the probability density function of the image density within the region. The first (or fourth) index value, var, takes a comparatively small value for the tumor pattern $P_1$ and takes a large value for the false positive $P_3$ such as a mammary gland pattern or a blood vessel pattern.

The second (or fifth) index value, con, represents the level of the image density value in the region. The second (or fifth) index value, con, takes a small value for a pattern having a low image density distribution as in the tumor pattern $P_1$. In cases where the image signal is the one which represents the radiation image displayed on a cathode ray tube (CRT) display device, the image signal corresponding to the region represents a high luminance, and therefore has a high signal level. In such cases, the second (or fifth) index value, con, takes a large value for the pattern having a high luminance distribution as in the tumor pattern $P_1$. In this embodiment, the image signal representing the image density is employed, and therefore the second (or fifth) index value, con, takes a small value for the tumor pattern $P_1$.

The third (or sixth) index value, asm, represents the level of uniformity of the image density values in the region. The third (or sixth) index value, asm, takes a small value for a pattern having an approximately uniform image density distribution as in the tumor pattern $P_1$.

In steps 6-1 (#6-1) and 6-4 (#6-4), the first and fourth index values, var, having been calculated for the first and second regions are compared respectively with threshold values Th1 and Th4, which have been determined previously on the basis of experiments and experience. Also, in steps 6-2 (#6-2) and 6-5 (#6-5), the second and fifth index values, con, having been calculated for the first and second regions are compared respectively with threshold values Th2 and TH5. Further, in steps 6-3 (#6-3) and 6-6 (#6-6), the third and sixth index values, asm, having been calculated for the first and second regions are compared respectively with threshold values Th3 and Th6.

Thereafter, in each of steps 7-1 (#7-1), 7-2 (#7-2), 7-3 (#7-3), 7-4 (#7-4), 7-5 (#7-5), and 7-6 (#7-6), in cases where the index value is found to represent the tumor pattern $P_1$ as a result of the comparison carried out in each step 6, a flag is set to be Fg=1. In cases where the index value is found not to represent the tumor pattern $P_1$, i.e. is found to represent the false positive $P_3$, as a result of the comparison carried out in each step 6, a flag is set to be Fg=0.

In steps 8 (#8) and 9 (#9), in Gases where all of flags Fg1, Fg2, Fg3, Fg4, Fg5, and Fg6 have been set to be "1," it is judged that the pattern is the tumor pattern $P_1$. In oases where at least one of the flags Fg1, Fg2, Fg3, Fg4, Fg5, and Fg6 has been set to be "0," it is judged that the pattern is the false positive $P_3$.

In this embodiment, the so-called AND technique is employed, wherein different threshold values are set for the respective feature measures (index values), and wherein the judgment as to whether the pattern is or is not the tumor pattern $P_1$ is made by judging whether all of the feature measures satisfy or do not satisfy the requirements with respect to the corresponding threshold values. However, the method for detecting an abnormal pattern in accordance with the present invention is not limited to the use of the AND technique. For example, a new rating function value may be obtained by defining the aforesaid six feature measures with a predetermined weight function, and a judgment may be made in accordance with the rating function value. As the rating function value defined with the weight function, for example, a Mahalanobis distance or a Fisher discriminating function may be employed.

Also, the judgment is made as to not only the first region containing the contour of the region to be detected but also the second region corresponding to only the contour of the region to be detected. This is because, also at the contour, a significant difference can be found between the normal pattern and the tumor pattern in the probability density function of the image density.

With the processing described above, the tumor pattern $P_1$, which could not be extracted, can be separated from the false positive $P_3$ and can thus be extracted. Thus only the definite prospective abnormal pattern, which has a high level of probability that it will be the true abnormal pattern, can be detected accurately.

Figure 7:
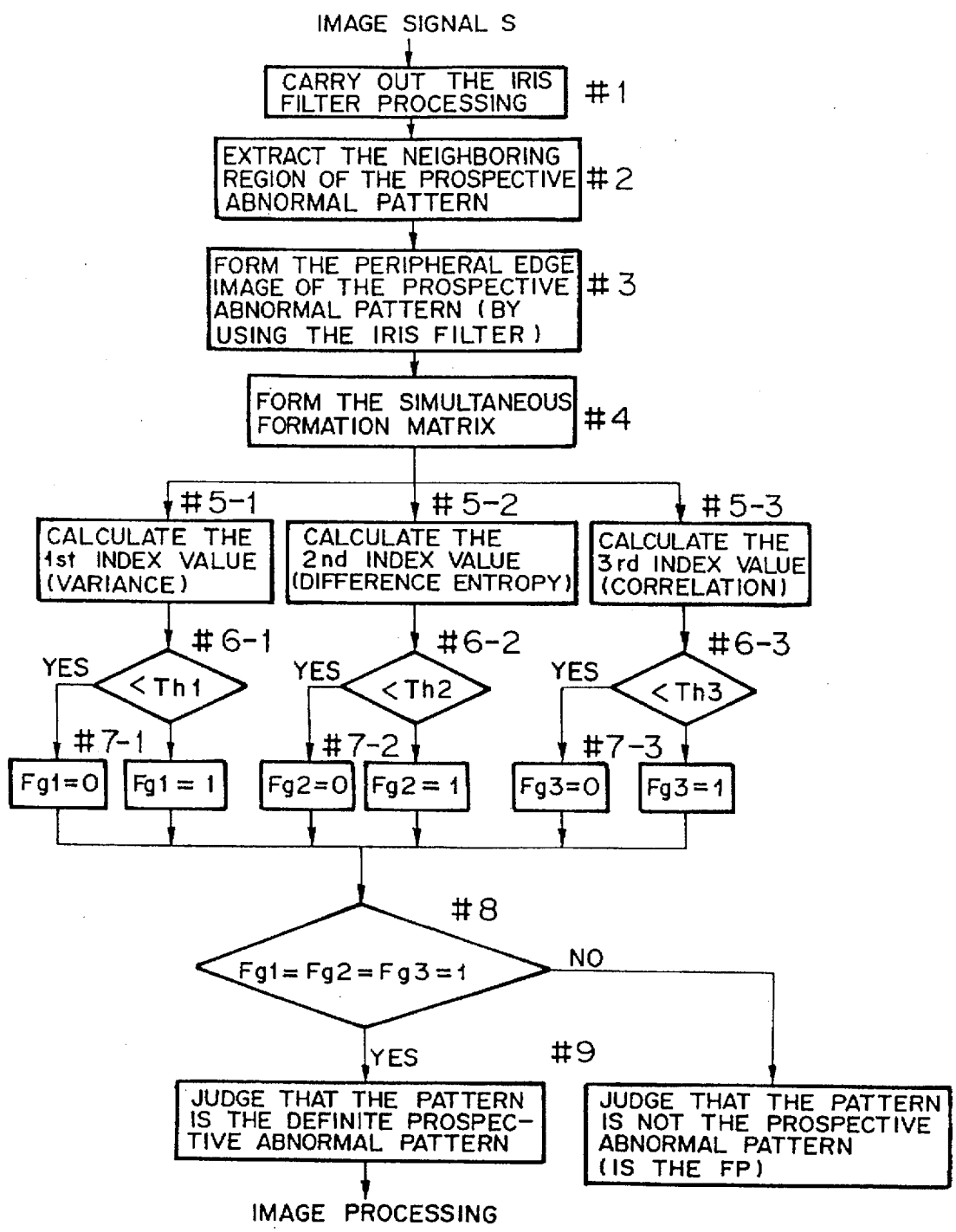
FIG. 7 is a flow chart showing the processing steps in a second embodiment of the method for detecting an abnormal pattern in accordance with the present invention.

FIG. 7 is a flow chart showing the processing steps in a second embodiment of the method for detecting an abnormal pattern in accordance with the present invention.

In the second embodiment, as in the first embodiment described above, the image signal representing the image density values is processed.

In this embodiment, in a first step (#1), an image signal, which represents a radiation image of an object (in this case, the mamma) P shown in FIG. 2A and represents image density values S, is received from an image read-out apparatus (not shown), or the like, and iris filter processing is carried out on the image density values S. With the iris filter processing, the tumor pattern $P_1$, which represents breast cancer, or the like, in the radiation image is detected.

The iris filter processing in the step 1 (#1) is carried out in the same manner as that in the aforesaid first embodiment.

In a step 2 (#2), for each of the tumor pattern $P_1$, which represents breast cancer, and the false positive $P_3$ having been detected with the iris filter processing, the image portion containing the pattern and the neighboring region is found as, for example, a square region.

Thereafter, in a step 3 (#3), as for the thus found region containing the prospective abnormal pattern, a peripheral (contour) edge image is formed by utilizing the aforesaid iris filter processing. How the peripheral edge image is formed will be described hereinbelow.

Specifically, with the iris filter processing employed in the step 1, the position of the point, which gives the maximum value of the degree of centralization Ci(n) on the i'th radial line extending radially from the picture element of interest, the maximum value being calculated with Formula (6), is detected. In Formula (5) or (5') and Formula (6), the value of n giving the maximum value of the degree of centralization Ci(n) falls within the range of Rmin to Rmax. However, in the processing of the step 3, the value of n is not limited to the aforesaid range.

Figure 8:
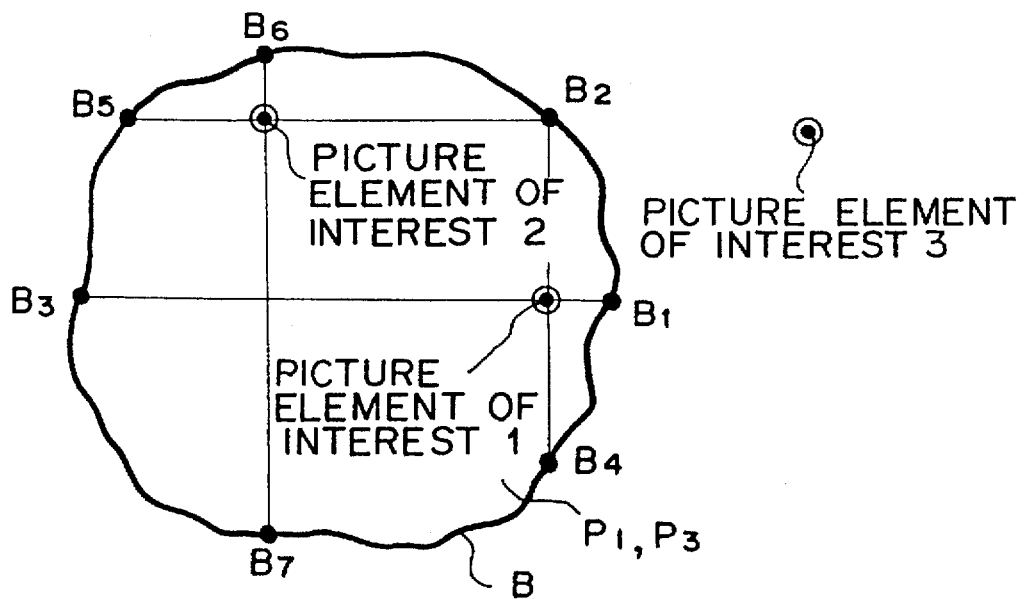
FIG. 8 is an explanatory view showing how an iris filter edge (IFED) image is formed.

As illustrated in FIG. 8, in cases where the picture element of interest is located in the region inward from the tumor pattern $P_1$ or the false positive $P_3$, the value of n giving the maximum value of Formula (6) indicates the picture element, at which the i'th radial line intersects with the periphery B of the tumor pattern $P_1$ or the false positive $P_3$. For example, as for a picture element of interest 1 shown in FIG. 8, the value of n indicates picture elements $B_1$, $B_2$, $B_3$, and $B_4$. As for a picture element of interest 2 shown in FIG. 8, the value of n indicates picture elements $B_2$, $B_5$, $B_6$, and $B_7$.

In cases where the picture element of interest is located in the region outward from the tumor pattern $P_1$ or the false positive $P_3$, when the value of n indicates the picture element of interest itself, the value of Formula (6) takes the maximum value. Specifically, as for a picture element of interest 3, which is located in the region outward from the tumor pattern $P_1$ or the false positive $P_3$, the value of Formula (6) takes the maximum value when the value of n indicates the picture element of interest itself.

Figure 9:
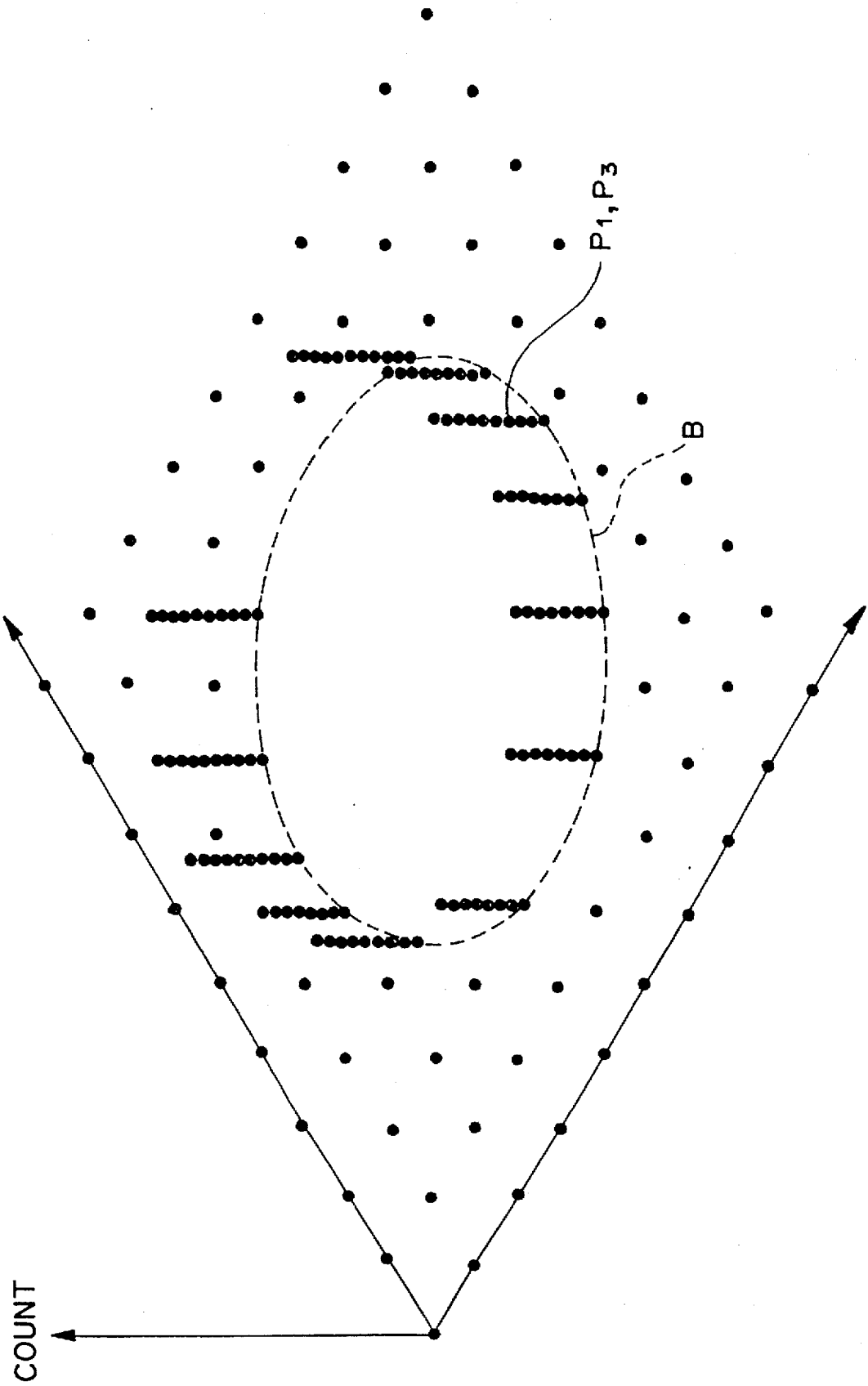
FIG. 9 is an explanatory view showing an IFED image.

All of the picture elements falling within the extracted region, which contains the abnormal pattern, are successively taken as the picture element of interest, and the number of the picture elements, which are associated with the maximum value of Formula (6), is counted. As a result, an image shown in FIG. 9 is obtained.

Specifically, as for all of the picture elements, which are located in the region outward from the tumor pattern $P_1$ or the false positive $P_3$, a count value of "1" is obtained. As for all of the picture elements, which are located in the region inward from the tumor pattern $P_1$ or the false positive $P_3$, a count value of "0" is obtained. Also, as for all of the picture elements, which are located on the periphery B of the tumor pattern $P_1$ or the false positive $P_3$, count values larger than 1 are obtained. The image representing the count values is defined as an iris filter image (IFED image). In this manner, in the step 3, the IFED image is formed.

In a step 4 (#4), the processing described below is carried out on the IFED image.

Figures 10, 11:
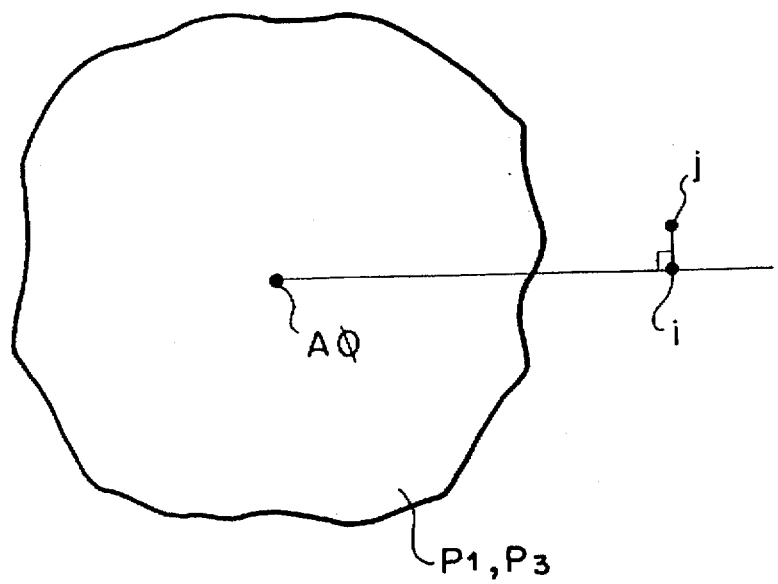
FIG. 10 is an explanatory view showing how a simultaneous formation matrix is formed in accordance with the IFED image.
FIG. 11 is an explanatory view showing a simultaneous formation matrix.

Specifically, as illustrated in FIG. 10, the position, at which the center of gravity AO on each of the tumor pattern $P_1$ and the false positive $P_3$ is located, is found. A radial line is extended from the position, at which the center of gravity AO is located. An arbitrary point lying on the radial line is represented by i, and a point, which is spaced a distance equal to the sum of the lengths of two picture elements from the point i along a line normal to the radial line, is represented by j.

The count value at the point i on the IFED image and the count value at the point j on the IFED image are counted up on a matrix shown in FIG. 11. Specifically, in cases where the point i is located in the region outward from the tumor pattern $P_1$ or the false positive $P_3$, the count value at the point i on the IFED image is "1." At this time, in cases where the point j is also located in the region outward from the tumor pattern $P_1$ or the false positive $P_3$, the count value at the point j on the IFED image is "1." In such cases, on the matrix shown in FIG. 11, "1" is counted in the cell, which is located at the intersection of an i-row "1" and a j-column "1."

In cases where the point i is located in the region inward from the tumor pattern $P_1$ or the false positive $P_3$, and the point j is also located in the region onward from the tumor pattern $P_1$ or the false positive $P_3$, the count values at the points i and j on the IFED image are "0." In such cases, on the matrix shown in FIG. 11, "1" is counted in the cell, which is located at the intersection of an i-row "0" and a j-column "0."

Also, in cases where the point i is located at the periphery B of the tumor pattern $P_1$ or the false positive $P_3$, and the point j is also located at the periphery B of the tumor pattern $P_1$ or the false positive $P_3$, the count value at the point i on the IFED image is, for example, "5," and the count value at the point j on the IFED image is, for example, "3." In such cases, on the matrix shown in FIG. 11, "1" is counted in the cell, which is located at the intersection of an i-row "5" and a j-column "3." The count value, which is counted up on the matrix, is cumulated. Specifically, when the point i on the IFED image, at which the count value is "5," and the corresponding point i on the IFED image, at which the count value is "3," is found again, "1" is added to the previously counted value "1" in the cell, which is located at the intersection of the i-row "5" and the j-column "3," and therefore "2" is stored in the cell.

The point i is an arbitrary point on the IFED image. The radial lines are set such that all of the picture elements of the IFED image may be taken as the point i, and the point i is searched along the respective radial lines. In this manner, the matrix shown in FIG. 11 is completed. The matrix is referred to as the simultaneous formation matrix (or the simultaneous incidence matrix). In this manner, in the step 4 (#4), the simultaneous formation matrix Pg(x, y) is completed.

The tumor pattern $P_1$ has the characteristics of the shape of the tumor pattern such that the periphery of the tumor pattern $P_1$ has an approximately circular shape. Also, the points i and j are very close to each other. Therefore, in cases where the prospective abnormal pattern is the tumor pattern $P_1$, there is a high level of probability that, when the point i is located at the periphery of the tumor pattern $P_1$ (i.e., when the count value at the point i on the IFED image is larger than 1), the point j will also be located at the periphery of the tumor pattern $P_1$ (i.e., the count value at the point j on the IFED image will be larger than 1).

On the other hand, in cases where the prospective abnormal pattern is the false positive $P_3$, as in the pattern at which two blood vessel patterns intersect each other, it is very rare that the false positive $P_3$ will have a circular periphery. Therefore, even if the points i and j are close to each other, when the point i is located at the periphery of the false positive $P_3$, the point j will not necessarily be located at the periphery of the false positive $P_3$. In such cases, the probability that the point j will also be located at the periphery of the false positive $P_3$ is markedly low.

Therefore, significant differences are found between the tumor pattern $P_1$ and the false positive $P_3$ in the characteristic values of the simultaneous formation matrix Pg(x, y). The characteristic values of the simultaneous formation matrix are herein referred to as the edge information. In steps 5-1 (#5-1), 5-2 (#5-2), and 5-3 (#5-3), as the edge information, the following are calculated respectively: (i) a first index value, var, which represents the variance with respect to the simultaneous formation matrix and is calculated with Formula (12), (ii) a second index value, dfe, which represents the difference entropy with respect to the simultaneous formation matrix and is calculated with Formula (13), and (iii) a third index value, cor, which represents the correlation with respect to the simultaneous formation matrix and is calculated with Formula (14). As will be described later, it is also possible to employ a fourth index value, idm, which represents the inverse difference moment with respect to the simultaneous formation matrix and is calculated with Formula (15), and a fifth index value, se, which represents the sum entropy with respect to the simultaneous formation matrix and is calculated with Formula (16).

$$var = \sum_i \sum_j \{(i - \mu_x)^2 \cdot P_g(i,j)\} \quad (12)$$

$$dfe = \sum_k \{P_{x-y}(k) \cdot \log|P_{x-y}(k)|\} \quad (13)$$

$$cor = \sum_i \sum_j [\{i \cdot j \cdot P_g(i,j) - \mu_x \cdot \mu_y\}/(\sigma_x \cdot \sigma_y)] \quad (14)$$

$$idm = \sum_i \sum_j [P_g(i,j)/\{1 + (i-j)^2\}] \quad (15)$$

$$se = -\sum_k [P_{x+y}(k) \cdot \log\{P_{x+y}(k)\}] \quad (16)$$

wherein $$\mu_x = \sum_i \{i \cdot P_x(i)\}, \mu_y = \sum_j \{j \cdot P_y(j)\}$$

$$P_{x-y}(k) = \sum_i \sum_j P_g(i,j), k = |i - j|$$

$$P_{x+y}(k) = \sum_i \sum_j P_g(i,j), k = i + j$$

$$\sigma_x^2 = \sum_i (i - \mu_x)^2 \cdot P_x(i)$$

$$\sigma_y^2 = \sum_j (j - \mu_y)^2 \cdot P_y(j)$$

Px(i) represents the projection distribution along the j direction, i. e., $$P_x(i) = \sum_j P_g(i,j)$$

and Py(j) represents the projection distribution along the i direction, i.e., $$P_y(j) = \sum_i P_g(i,j)$$

Each of the first index value, var, the second index value, dfe, and the third index value, cor, with respect to the simultaneous formation matrix takes a comparatively large value for the tumor pattern $P_1$ and takes a small value for the false positive $P_3$, such as a mammary gland pattern or a blood vessel pattern.

In a step 6-1 (#6-1), the first index value, var, having been calculated for each region is compared with a threshold value Th1, which has been determined previously on the basis of experiments and experience. Also, in a step 6-2 (#6-2), the second index value, dfe, having been calculated for the region is compared with a threshold value Th2. Further, in a step 6-3 (#6-3), the third index value, cor, having been calculated for the region is compared with a threshold value Th3.

Thereafter, in each of steps 7-1 (#7-1), 7-2 (#7-2), and 7-3 (#7-3), in cases where the index value is found to represent the tumor pattern $P_1$ as a result of the comparison carried out in each step 6, a flag is set to be Fg=1. In cases where the index value is found not to represent the tumor pattern $P_1$, i e. is found to represent the false positive $P_3$, as a result of the comparison carried out in each step 6, a flag is set to be Fg=0.

In steps 8 (#8) and 9 (#9), in cases where all of flags Fg1, Fg2, and Fg3, have been set to be "1," it is judged that the pattern is the tumor pattern $P_1$. In cases where at least one of the flags Fg1, Fg2, and Fg3 has been set to be "0," it is judged that the pattern is the false positive $P_3$. The technique, wherein only when all of a plurality of the feature measures (index values) satisfy the requirements with respect to the corresponding threshold values, it is judged that the pattern is the tumor pattern $P_1$, is referred to as the AND technique.

In this embodiment, only the variance, the difference entropy, and the correlation are employed as the edge information. As described above, as the other edge information, it is also possible to employ the fourth index value, idm, which represents the inverse difference moment with respect to the simultaneous formation matrix and is calculated with Formula (15), and the fifth index value, se, which represents the sum entropy with respect to the simultaneous formation matrix and is calculated with Formula (16). The fourth index value, idm, with respect to the simultaneous formation matrix takes a comparatively small value for the tumor pattern $P_1$ and takes a large value for the false positive $P_3$, such as a mammary gland pattern or a blood vessel pattern. The fifth index value, se, with respect to the simultaneous formation matrix takes a comparatively large value for the tumor pattern $P_1$ and takes a small value for the false positive $P_3$, such as a mammary gland pattern or a blood vessel pattern.

Also, a new rating function value may be obtained by defining an arbitrary number of the feature measures with a predetermined weight function, and a judgment may be made in accordance with the rating function value.

With the processing described above, the tumor pattern $P_1$, which could not be extracted, can be separated from the false positive $P_3$ and can thus be extracted. Thus only the definite prospective abnormal pattern, which has a high level of probability that it will be the true abnormal pattern, can be detected accurately.

In this embodiment, the point j is defined as the point, which is spaced a distance equal to the sum of the lengths of two picture elements from the point i along the line normal to the radial line on which the point i is set. The angle made between the line, on which the point j is located, and the radial line, on which the point i is set, and the distance of the point j from the point i may be altered in accordance with the size of the tumor pattern to be detected, or the like.

An embodiment, in which a new rating function value is obtained by defining an arbitrary number of the feature measures with a predetermined weight function, and a judgment as to whether the pattern is or is not a definite prospective abnormal pattern is made in accordance with the rating function value, will be described hereinbelow.

As described above, as the rating function value defined with the weight function, the Mahalanobis distance or the Fisher discriminating function should preferably be employed. FIG. 13 is a flow chart showing the processing steps in an embodiment of the method for detecting an abnormal pattern in accordance with the present invention, wherein a judgment is made with the Mahalanobis distance.

In this embodiment, the processing of a step 1 to a step 4 is the same as the processing of the step 1 to the step 4 shown in FIG. 7.

In a step 5 (#5), as the characteristic values of the simultaneous formation matrix formed in the step 4, which constitute the edge information, the following index values are calculated: (i) the first index value, var, which represents the variance with respect to the simultaneous formation matrix and is calculated with Formula (12), (ii) the second index value, dfe, which represents the difference entropy with respect to the simultaneous formation matrix and is calculated with Formula (13), (iii) the third index value, cor, which represents the correlation with respect to the simultaneous formation matrix and is calculated with Formula (14), (iv) the fourth index value, idm, which represents the inverse difference moment with respect to the simultaneous formation matrix and is calculated with Formula (15), and (v) the fifth index value, se, which represents the sum entropy with respect to the simultaneous formation matrix and is calculated with Formula (16).

In a step 6 (#6), the five index values are allocated to five-dimensional different axes (x1, x2, x3, x4, and x5). For example, the index values var, dfe, cot, idm, and se are allocated respectively to the axes x1, x2, x3, x4, and x5. The vector $\vec{x}$ composed of the five-order elements is set.

Thereafter, in a step 7 (#7), the Mahalanobis distance Dm1 with respect to a pattern class, which represents the normal pattern, and the Mahalanobis distance Dm2 with respect to a pattern class, which represents the abnormal pattern, are calculated with Formula (17).

$$Dmi = (\vec{x} - \vec{mi}) t \Sigma_i^{-1} (\vec{x} - \vec{mi}) \tag{17}$$

wherein $\Sigma i$ represents the covariance matrix of the pattern class (pattern classification between the normal pattern of i=1 and the abnormal pattern of i=2) wi, i.e., $$\Sigma_i = (1/Ni) \sum_{x \in wi} (\vec{x} - \vec{mi})(\vec{x} - \vec{mi})^t$$

t represents the transposed vector (row vector), $\vec{x}$ represents the vector of the feature measure x, i.e., $$\vec{x} = (x1, x2, \ldots, xN)$$

$\Sigma_i^{-1}$ represents the inverse matrix of $\Sigma i$, and $\vec{mi}$ represents the mean value of the pattern classes wi, i.e., $$\vec{mi} = (1/Ni) \sum_{x \in wi} \vec{x}$$

Each of the pattern class of the normal pattern and the pattern class of the abnormal pattern represents the class of the pattern space, which is set in accordance with the results of experiments carried out on a plurality of prospective abnormal patterns and is defined by the vector $\vec{e}$ with respect to each of the normal pattern and the abnormal pattern. For example, the pattern class w1 is formed with the mean value of the vector $\vec{x}$ with respect to the normal pattern, and the pattern class w2 is formed with the mean value of the vector $\vec{x}$ with respect to the abnormal pattern.

In this manner, a calculation is made to find the Mahalanobis distance Dm1 between the pattern class, which represents the normal pattern and has been set previously, and the pattern class (the aforesaid vector $\vec{x}$), which represents the prospective abnormal pattern to be detected. Also, a calculation is made to find the Mahalanobis distance Dm2 between the pattern class, which represents the abnormal pattern and has been set previously, and the pattern class (the aforesaid vector $\vec{x}$), which represents the prospective abnormal pattern to be detected. Thereafter, in a step 8 (#8), the Mahalanobis distance Dm1 with respect to the pattern class, which represents the normal pattern, and the Mahalanobis distance Dm2 with respect to the pattern class, which represents the abnormal pattern, are compared with each other. In a step 9 (#9), in cases where the Mahalanobis distance Dm1 is not longer than the Mahalanobis distance Dm2, it is judged that the detected pattern is not a prospective abnormal pattern, i.e. is the false positive. In cases where the Mahalanobis distance Dm1 is longer than the Mahalanobis distance Dm2, it is judged that the detected pattern is a definite prospective abnormal pattern.

In this manner, the definite prospective abnormal pattern can be detected also with the detection method wherein the rating function value is employed.

Figure 12:
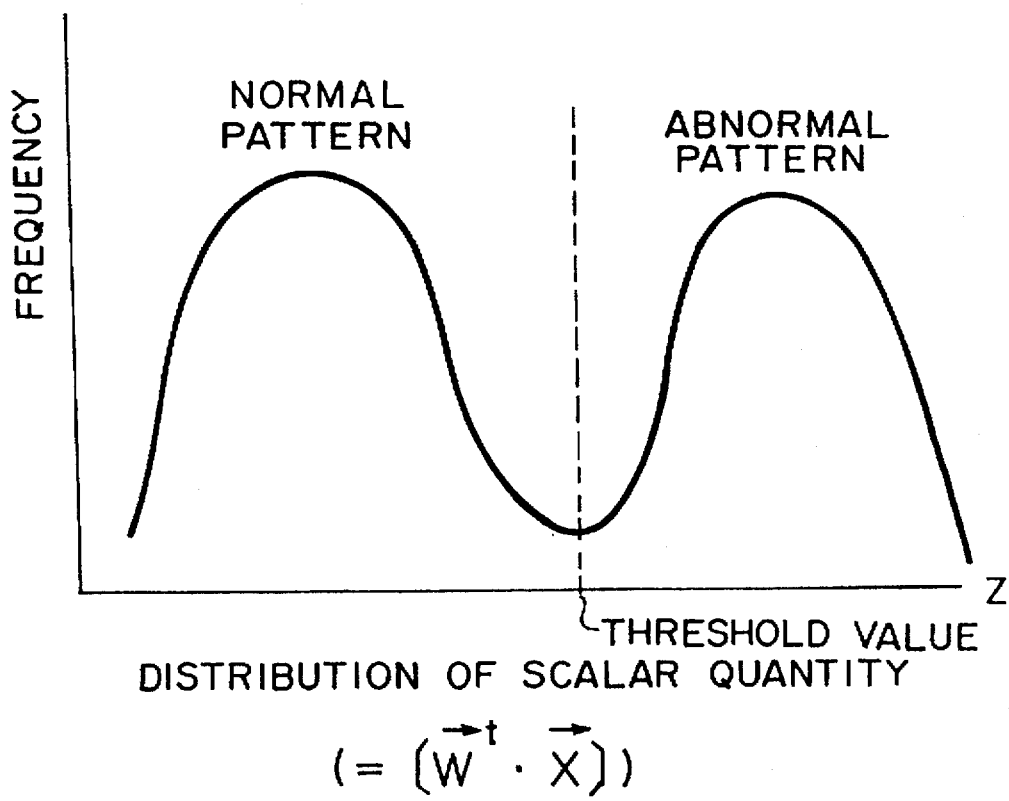
FIG. 12 is a graph showing a distribution of scalar quantity, the graph serving as an aid in explaining how a threshold value is set in accordance with the distribution of the scalar quantity in cases where a Fisher discriminating function is to be utilized.

In cases where the Fisher discriminating function is employed as the rating function value, in the step 7 shown in FIG. 13, the scalar quantity is calculated with Formula (21) shown above with respect to the prospective abnormal pattern to be detected. Also, as illustrated in FIG. 12, a threshold value is set in accordance with the results having been obtained previously by experimentally investigating the distribution of the scalar quantity with respect to a plurality of prospective abnormal patterns. The scalar quantity, which has been calculated with Formula (21) with respect to the prospective abnormal pattern to be detected, is compared with the threshold value, and the definite prospective abnormal pattern may be detected in accordance with the results of the comparison.

In the aforesaid embodiment wherein the rating function value is employed, only the index values constituting the edge information are utilized. Alternatively, only the index values constituting the probability density function information may be utilized. As another alternative, an arbitrary number of the index values, which are among the index values constituting the probability density function information, and an arbitrary number of the index values, which are among the index values constituting the edge information, may be utilized, and the rating function value may thereby be set.

Also, in the embodiments described above, the iris filter processing is employed as the technique for detecting prospective abnormal patterns. However, the method for detecting an abnormal pattern in accordance with the present invention is not limited to the use of the iris filter processing, and any of techniques, with which prospective abnormal patterns, such as prospective tumor patterns, can be detected, can be employed.

The present invention will further be illustrated by the following nonlimitative experimental example.

Example

In this example, the first embodiment of the method for detecting an abnormal pattern in accordance with the present invention, which is shown in FIG. 1, was employed.

Experiments were carried out by using mammography data base images in a system for computer aided diagnosis of medical images (Bulletin of The Japanese Society of Computer Aided Diagnosis of Medical images, "Mammography Data Base," The Japan Society of Computer Aided Diagnosis of Medical Images, 1995). In the experiments, 51 images, each of which was constituted of 1,225×1,000 picture elements and had a spatial resolution of 0.2 mm/pixel and a luminance resolution of 10 bits, were used. Of these images, 12 images contained tumor patterns. The number of the tumor patterns was 12.

With the processing for detecting prospective tumor patterns by using an iris filter, 152 prospective tumor patterns were detected from these images. All of the 12 true tumor patterns were contained in the 152 prospective tumor patterns.

As for the 152 regions, the aforesaid first embodiment of the method for detecting an abnormal pattern in accordance with the present invention was carried out. The results shown in Table 1 were obtained.

TABLE 1

|  | Conventional Technique | | Present Invention | |
| --- | --- | --- | --- | --- |
|  | Judged to be tumor images | Judged to be normal images | Judged to be tumor images | Judged to be normal images |
| Tumor images | 12/12 100% | 0/12 0% | 12/12 100% | 0/12 0% |
| Normal images | 7/39 18.4% | 31/39 81.6% | 4/39 9.75% | 35/39 90.24% |

As clear from Table 1, with the first embodiment of the method for detecting an abnormal pattern in accordance with the present invention, the rate, with which the normal image was judged to be the normal image, was higher than 90%, and thus comparatively good results were obtained.

Further, in order for the effects of the first embodiment of the method for detecting an abnormal pattern in accordance with the present invention to be confirmed, the first embodiment was carried out on other 220 images. As a result, as for 16 images containing malignant tumor patterns and 17 images containing benign tumor patterns, the rate, with which the malignant tumor patterns were detected, was 100%, and quasi-positive patterns were found at a rate of 0.6 pattern per image. Thus good effects were obtained.

What is claimed is:

1. A method for detecting an abnormal pattern in a radiation image, wherein prospective abnormal patterns in a radiation image of an object are detected in accordance with an image signal representing the radiation image, the method comprising the steps of:
   i) forming a probability density function of the image signal, which corresponds to a region, that is inward from a contour of each of the prospective abnormal patterns having been detected, and a neighboring region,
   ii) obtaining probability density function information in accordance with said probability density function, and
   iii) detecting a definite prospective abnormal pattern, which is among the prospective abnormal patterns having been detected, in accordance with said probability density function information.

2. A method as defined in claim 1 wherein the detection of the prospective abnormal patterns is carried out with iris filter processing.

3. A method as defined in claim 1 wherein said probability density function information is a new rating function value, which is obtained by combining at least two index values selected from the group consisting of a first index value representing a variance of said probability density function, a second index value representing a contrast of said probability density function, and a third index value representing an angular moment of said probability density function, and
   said definite prospective abnormal pattern is detected in accordance with said rating function value.

4. A method as defined in claim 3 wherein the detection of the prospective abnormal patterns is carried out with iris filter processing.

5. A method as defined in claim 1 wherein said probability density function information is at least one index value selected from the group consisting of a first index value representing a variance of said probability density function, a second index value representing a contrast of said probability density function, and a third index value representing an angular moment of said probability density function, and
   said definite prospective abnormal pattern is detected in accordance with at least one index value selected from the group consisting of said first, second, and third index values.

6. A method as defined in claim 5 wherein the detection of the prospective abnormal patterns is carried out with iris filter processing.

7. A method for detecting an abnormal pattern in a radiation image, wherein prospective abnormal patterns in a radiation image of an object are detected in accordance with an image signal representing the radiation image, the method comprising the steps of:
   i) forming a probability density function of the image signal, which corresponds to a region, that is inward from a contour of each of the prospective abnormal patterns having been detected, and a neighboring region,
   ii) obtaining probability density function information in accordance with said probability density function,
   iii) obtaining edge information of a contour of each of the prospective abnormal patterns having been detected, and
   iv) detecting a definite prospective abnormal pattern, which is among the prospective abnormal patterns having been detected, in accordance with said probability density function information and said edge information.

8. A method as defined in claim 7 wherein the detection of the prospective abnormal patterns is carried out with iris filter processing.

9. A method as defined in claim 7 wherein said probability density function information is at least one index value selected from the group consisting of a first index value representing a variance of said probability density function, a second index value representing a contrast of said probability density function, and a third index value representing an angular moment of said probability density function,
   said edge information is at least one index value selected from the group consisting of a fourth index value representing a variance with respect to a simultaneous formation matrix having been obtained by the utilization of iris filter processing, a fifth index value representing a difference entropy with respect to said simultaneous formation matrix, a sixth index value representing a correlation with respect to said simultaneous formation matrix, a seventh index value representing an inverse difference moment with respect to said simultaneous formation matrix, and an eighth index value representing a sum entropy with respect to said simultaneous formation matrix,
   a new rating function value is obtained by combining at least one index value, which is selected from the group consisting of said first, second, and third index values, and at least one index value, which is selected from the group consisting of said fourth, fifth, sixth, seventh, and eighth index values, and
   said definite prospective abnormal pattern is detected in accordance with said rating function value.

10. A method as defined in claim 9 wherein the detection of the prospective abnormal patterns is carried out with iris filter processing.

11. A method as defined in claim 7 wherein said probability density function information is at least one index value selected from the group consisting of a first index value representing a variance of said probability density function, a second index value representing a contrast of said probability density function, and a third index value representing an angular moment of said probability density function, said edge information is at least one index value selected from the group consisting of a fourth index value representing a variance with respect to a simultaneous formation matrix having been obtained by the utilization of iris filter processing, a fifth index value representing a difference entropy with respect to said simultaneous formation matrix, a sixth index value representing a correlation with respect to said simultaneous formation matrix, a seventh index value representing an inverse difference moment with respect to said simultaneous formation matrix, and an eighth index value representing a sum entropy with respect to said simultaneous formation matrix, and said definite prospective abnormal pattern is detected in accordance with at least one index value, which is selected from the group consisting of said first, second, and third index values, and at least one index value, which is selected from the group consisting of said fourth, fifth, sixth, seventh, and eighth index values.

12. A method as defined in claim 11 wherein the detection of the prospective abnormal patterns is carried out with iris filter processing.

13. A method for detecting an abnormal pattern in a radiation image, wherein prospective abnormal patterns in a radiation image of an object are detected in accordance with an image signal representing the radiation image, the method comprising the steps of:

i) obtaining edge information of a contour of each of the prospective abnormal patterns having been detected, and ii) detecting a definite prospective abnormal pattern, which is among the prospective abnormal patterns having been detected, in accordance with said edge information.

14. A method as defined in claim 13 wherein the detection of the prospective abnormal patterns is carried out with iris filter processing.

15. A method as defined in claim 13 wherein said edge information is at least one index value selected from the group consisting of a first index value representing a variance with respect to a simultaneous formation matrix having been obtained by the utilization of iris filter processing, a second index value representing a difference entropy with respect to said simultaneous formation matrix, a third index value representing a correlation with respect to said simultaneous formation matrix, a fourth index value representing an inverse difference moment with respect to said simultaneous formation matrix, and a fifth index value representing a sum entropy with respect to said simultaneous formation matrix, and said definite prospective abnormal pattern is detected in accordance with at least one index value selected from the group consisting of said first, second, third, fourth, and fifth index values.

16. A method as defined in claim 15 wherein the detection of the prospective abnormal patterns is carried out with iris filter processing.

17. A method as defined in claim 13 wherein said edge information is a new rating function value, which is obtained by combining at least two index values selected from the group consisting of a first index value representing a variance with respect to a simultaneous formation matrix having been obtained by the utilization of iris filter processing, a second index value representing a difference entropy with respect to said simultaneous formation matrix, a third index value representing a correlation with respect to said simultaneous formation matrix, a fourth index value representing an inverse difference moment with respect to said simultaneous formation matrix, and a fifth index value representing a sum entropy with respect to said simultaneous formation matrix, and said definite prospective abnormal pattern is detected in accordance with said rating function value.

18. A method as defined in claim 17 wherein the detection of the prospective abnormal patterns is carried out with iris filter processing.

* * * * *